United States Patent
Garbin et al.

(10) Patent No.: US 11,793,394 B2
(45) Date of Patent: Oct. 24, 2023

(54) STEERABLE ENDOSCOPE WITH CONTINUUM MANIPULATOR

(71) Applicant: Vanderbilt University, Nashville, TN (US)

(72) Inventors: Nicolo Garbin, Nashville, TN (US); Pietro Valdastri, Leeds (GB); Keith L. Obstein, Nashville, TN (US); Nabil Simaan, Nashville, TN (US); Piotr Robert Slawinski, Lincoln, NE (US)

(73) Assignees: Vanderbilt University, Nashville, TN (US); University of Leeds, Leeds (GB)

( * ) Notice: Subject to any disclaimer, the term of this patent is extended or adjusted under 35 U.S.C. 154(b) by 723 days.

(21) Appl. No.: 16/465,621

(22) PCT Filed: Dec. 1, 2017

(86) PCT No.: PCT/US2017/064271
§ 371 (c)(1),
(2) Date: May 31, 2019

(87) PCT Pub. No.: WO2018/102718
PCT Pub. Date: Jun. 7, 2018

(65) Prior Publication Data
US 2020/0015657 A1    Jan. 16, 2020

Related U.S. Application Data

(60) Provisional application No. 62/507,110, filed on May 16, 2017, provisional application No. 62/429,675, filed on Dec. 2, 2016.

(51) Int. Cl.
*A61M 25/01* (2006.01)
*A61B 1/005* (2006.01)
(Continued)

(52) U.S. Cl.
CPC .......... *A61B 1/0055* (2013.01); *A61B 1/0052* (2013.01); *A61B 1/2733* (2013.01);
(Continued)

(58) Field of Classification Search
CPC .......... A61M 25/0133; A61M 25/0147; A61M 25/0152; A61M 25/0155; A61M 25/0026;
(Continued)

(56) References Cited

U.S. PATENT DOCUMENTS 2,286,571 A    6/1942  Pollard
2,988,237 A    6/1961  Devol
(Continued)

FOREIGN PATENT DOCUMENTS

CN    1219855 A    6/1999
CN    1649537 A    8/2005
(Continued)

OTHER PUBLICATIONS

Chinese Patent Office Action and Search Report for Application No. 201780085425.9 dated Mar. 29, 2021 (7 pages including statement of relevance).
(Continued)

*Primary Examiner* — Katherine H Schwiker
*Assistant Examiner* — Anna E Goldberg-Richmeier
(74) *Attorney, Agent, or Firm* — Michael Best & Friedrich LLP

(57) ABSTRACT

A steerable endoscope system includes a continuum manipulator, a plurality of syringes, and a steerable tip. The continuum manipulator includes a plurality of spaced discs and a plurality of backbones each extending through all discs. A bending movement of the continuum manipulator changes a varying linear displacement of each backbone. Each backbone is further coupled to a different one of the syringes such that the linear displacement of each backbone pushes or
(Continued)

pulls a piston of the corresponding syringe by a varying amount. The steerable tip includes a plurality of bellows each pneumatically coupled to a different syringe such that movement of the piston of a syringe causes the corresponding bellow to inflate or deflate. Because the distal end of each bellow is fixedly coupled to the same end effector, variations in the amount of inflation or deflation on each bellow causes a bending of the steerable tip.

15 Claims, 5 Drawing Sheets

(51) Int. Cl.
  *A61B 1/273* (2006.01)
  *A61M 25/00* (2006.01)
(52) U.S. Cl.
  CPC .... *A61M 25/0084* (2013.01); *A61M 25/0138* (2013.01); *A61M 25/0155* (2013.01); *A61M 2025/0085* (2013.01)
(58) Field of Classification Search
  CPC ...... A61M 25/0067; A61M 2025/0175; A61M 2025/0024; A61M 2025/0025; A61B 1/0055; A61B 1/0052
  See application file for complete search history.

(56) References Cited

U.S. PATENT DOCUMENTS

| | | | |
|---|---|---|---|
| 3,580,099 A | 5/1971 | Mosher | |
| 3,727,531 A | 4/1973 | Baab | |
| 3,802,743 A | 4/1974 | Hermanns | |
| 4,744,264 A | 5/1988 | Milenkovic | |
| 4,795,296 A | 1/1989 | Jau | |
| 4,802,461 A | 2/1989 | Cho | |
| 4,838,859 A * | 6/1989 | Strassmann | A61B 1/00156 604/95.03 |
| 4,998,527 A | 3/1991 | Meyer | |
| 5,007,907 A | 4/1991 | Nishigaki et al. | |
| 5,046,375 A | 9/1991 | Salisbury, Jr. | |
| 5,133,713 A | 7/1992 | Huang et al. | |
| 5,201,731 A | 4/1993 | Hakky | |
| 5,231,989 A | 8/1993 | Middleman et al. | |
| 5,307,804 A | 5/1994 | Bonnet | |
| 5,337,732 A | 8/1994 | Grundfest et al. | |
| 5,345,937 A | 9/1994 | Middleman et al. | |
| 5,386,741 A | 2/1995 | Rennex | |
| 5,397,323 A | 3/1995 | Taylor | |
| 5,410,638 A | 4/1995 | Colgate | |
| 5,480,406 A | 1/1996 | Nolan et al. | |
| 5,662,587 A | 9/1997 | Grundfest et al. | |
| 5,749,828 A | 5/1998 | Solomon et al. | |
| 5,897,488 A | 4/1999 | Ueda | |
| 5,906,591 A | 5/1999 | Dario et al. | |
| 6,113,593 A | 9/2000 | Tu et al. | |
| 6,197,017 B1 | 3/2001 | Brock et al. | |
| 6,309,346 B1 | 10/2001 | Farhadi | |
| 6,312,435 B1 | 11/2001 | Wallace et al. | |
| 6,485,409 B1 * | 11/2002 | Voloshin | A61M 25/0119 600/115 |
| 6,533,720 B1 | 3/2003 | Dhindsa | |
| 6,554,844 B2 | 4/2003 | Lee et al. | |
| 6,669,711 B1 | 12/2003 | Noda | |
| 6,676,684 B1 | 1/2004 | Morley | |
| 6,692,485 B1 | 2/2004 | Brock | |
| 6,817,974 B2 | 11/2004 | Cooper et al. | |
| 6,824,544 B2 | 11/2004 | Boebel et al. | |
| 6,837,892 B2 | 1/2005 | Shoham | |
| 6,843,793 B2 | 1/2005 | Brock et al. | |
| 6,858,005 B2 | 2/2005 | Ohline et al. | |
| 6,860,878 B2 | 3/2005 | Brock | |
| 6,949,106 B2 | 9/2005 | Brock et al. | |
| 6,971,989 B2 | 12/2005 | Yossepowitch | |
| 7,021,173 B2 | 4/2006 | Stoianovici et al. | |
| 7,099,745 B2 | 8/2006 | Ebert | |
| 7,147,650 B2 | 12/2006 | Lee | |
| 7,214,230 B2 | 5/2007 | Brock et al. | |
| 7,235,089 B1 | 6/2007 | McGuckin, Jr. | |
| 7,316,681 B2 | 1/2008 | Madhani et al. | |
| 7,391,173 B2 | 6/2008 | Schena | |
| 7,682,319 B2 | 3/2010 | Martin et al. | |
| 7,699,835 B2 * | 4/2010 | Lee | A61B 34/35 606/1 |
| 7,787,681 B2 | 8/2010 | Zhang et al. | |
| 7,794,393 B2 | 9/2010 | Larsen | |
| 7,822,249 B2 | 10/2010 | Garty et al. | |
| 7,837,615 B2 | 11/2010 | Le et al. | |
| 7,854,738 B2 | 12/2010 | Lee et al. | |
| 7,887,549 B2 | 2/2011 | Wenderow et al. | |
| 7,959,557 B2 | 6/2011 | Weitzner et al. | |
| 8,025,635 B2 | 9/2011 | Eaton et al. | |
| 8,062,214 B2 | 11/2011 | Shener et al. | |
| 8,088,101 B2 | 1/2012 | Chang et al. | |
| 8,114,062 B2 | 2/2012 | Muni et al. | |
| 8,116,886 B2 | 2/2012 | Simaan et al. | |
| 8,172,828 B2 | 5/2012 | Chang et al. | |
| 8,303,576 B2 | 11/2012 | Brock | |
| 8,311,626 B2 | 11/2012 | Hlavka et al. | |
| 8,337,521 B2 | 12/2012 | Cooper et al. | |
| 8,343,141 B2 | 1/2013 | Madhani et al. | |
| 8,365,633 B2 | 2/2013 | Simaan et al. | |
| 8,372,019 B2 | 2/2013 | Goldenberg et al. | |
| 8,377,077 B2 | 2/2013 | Reis | |
| 8,409,234 B2 | 4/2013 | Stahler et al. | |
| 8,414,505 B1 | 4/2013 | Weitzner et al. | |
| 8,414,598 B2 | 4/2013 | Brock et al. | |
| 8,425,402 B2 | 4/2013 | Annest et al. | |
| 8,425,408 B2 | 4/2013 | Boulais et al. | |
| 8,444,549 B2 | 5/2013 | Viola et al. | |
| 8,460,236 B2 | 6/2013 | Roelle et al. | |
| 8,480,618 B2 | 7/2013 | Wenderow et al. | |
| 8,486,053 B2 | 7/2013 | Niemeyer | |
| 8,498,691 B2 | 7/2013 | Moll et al. | |
| 8,504,201 B2 | 8/2013 | Moll et al. | |
| 8,545,551 B2 | 10/2013 | Loulmet | |
| 8,551,115 B2 | 10/2013 | Steger et al. | |
| 8,585,731 B2 | 11/2013 | Abbate et al. | |
| 8,655,431 B2 | 2/2014 | Joos et al. | |
| 8,721,530 B2 | 5/2014 | Ohline et al. | |
| 8,864,757 B2 | 10/2014 | Klimovitch et al. | |
| 9,333,650 B2 | 5/2016 | Bajo et al. | |
| 9,549,720 B2 | 1/2017 | Simaan et al. | |
| 9,591,964 B2 | 3/2017 | Choset et al. | |
| 2001/0031983 A1 | 10/2001 | Brock et al. | |
| 2002/0032365 A1 | 3/2002 | Hasegawa et al. | |
| 2002/0120252 A1 | 8/2002 | Brock et al. | |
| 2003/0120305 A1 | 6/2003 | Jud et al. | |
| 2003/0135204 A1 | 7/2003 | Lee et al. | |
| 2003/0181785 A1 * | 9/2003 | Viebach | F15B 7/001 600/152 |
| 2004/0116906 A1 | 6/2004 | Lipow | |
| 2004/0176751 A1 | 9/2004 | Weitzner et al. | |
| 2005/0043718 A1 | 2/2005 | Madhani et al. | |
| 2005/0054900 A1 | 3/2005 | Mawn et al. | |
| 2005/0059960 A1 | 3/2005 | Simaan et al. | |
| 2005/0228440 A1 | 10/2005 | Brock et al. | |
| 2006/0036182 A1 | 2/2006 | Daniels et al. | |
| 2006/0047302 A1 | 3/2006 | Ortiz et al. | |
| 2006/0058861 A1 | 3/2006 | Gibson et al. | |
| 2006/0079884 A1 | 4/2006 | Manzo et al. | |
| 2006/0089535 A1 | 4/2006 | Raz et al. | |
| 2006/0156851 A1 | 7/2006 | Jacobsen et al. | |
| 2006/0241414 A1 | 10/2006 | Nowlin et al. | |
| 2006/0258938 A1 | 11/2006 | Hoffman et al. | |
| 2007/0021737 A1 * | 1/2007 | Lee | A61B 17/2909 606/1 |
| 2007/0197939 A1 | 8/2007 | Wallace et al. | |
| 2007/0225787 A1 | 9/2007 | Simaan et al. | |
| 2007/0255109 A1 | 11/2007 | Stein et al. | |
| 2007/0276430 A1 * | 11/2007 | Lee | A61B 17/29 606/205 |

(56) References Cited

U.S. PATENT DOCUMENTS

| | | |
|---|---|---|
| 2008/0009838 A1 | 1/2008 | Schena et al. |
| 2008/0033240 A1 | 2/2008 | Hoffman et al. |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0114492 A1 | 5/2008 | Miegel et al. |
| 2008/0179301 A1 | 7/2008 | Garty et al. |
| 2008/0181473 A1 | 7/2008 | Garty et al. |
| 2008/0188800 A1 | 8/2008 | Bencini et al. |
| 2008/0243063 A1 | 10/2008 | Camarillo |
| 2008/0243064 A1 | 10/2008 | Stahler et al. |
| 2008/0243106 A1 | 10/2008 | Coe et al. |
| 2008/0245173 A1 | 10/2008 | Schwerin et al. |
| 2008/0249536 A1 | 10/2008 | Stahler et al. |
| 2008/0262513 A1 | 10/2008 | Stahler et al. |
| 2008/0302200 A1 | 12/2008 | Tobey |
| 2009/0054222 A1 | 2/2009 | Zhang et al. |
| 2009/0076476 A1 | 3/2009 | Barbagli et al. |
| 2009/0076521 A1 | 3/2009 | Hansen |
| 2009/0088774 A1 | 4/2009 | Swarup et al. |
| 2009/0099420 A1 | 4/2009 | Woodley et al. |
| 2009/0171151 A1 | 7/2009 | Choset et al. |
| 2009/0216083 A1 | 8/2009 | Durant et al. |
| 2009/0275818 A1 | 11/2009 | Rau et al. |
| 2009/0275857 A1 | 11/2009 | Cabiri et al. |
| 2010/0010504 A1 | 1/2010 | Simaan et al. |
| 2010/0011900 A1 | 1/2010 | Burbank |
| 2010/0016852 A1 | 1/2010 | Manzo et al. |
| 2010/0030377 A1 | 2/2010 | Unsworth |
| 2010/0069719 A1 | 3/2010 | Wehrheim |
| 2010/0076269 A1 | 3/2010 | Makower |
| 2010/0079308 A1 | 4/2010 | Fabre et al. |
| 2010/0099951 A1 | 4/2010 | Laby et al. |
| 2010/0125165 A1 | 5/2010 | Torii |
| 2010/0152899 A1 | 6/2010 | Chang et al. |
| 2010/0210391 A9 | 8/2010 | Dinger |
| 2010/0256558 A1 | 10/2010 | Olson et al. |
| 2010/0331857 A1 | 12/2010 | Doyle et al. |
| 2010/0331858 A1 | 12/2010 | Simaan et al. |
| 2011/0015649 A1 | 1/2011 | Anvari et al. |
| 2011/0066160 A1 | 3/2011 | Simaan et al. |
| 2011/0071541 A1 | 3/2011 | Prisco et al. |
| 2011/0071542 A1 | 3/2011 | Prisco et al. |
| 2011/0071544 A1 | 3/2011 | Steger et al. |
| 2011/0125165 A1 | 5/2011 | Simaan et al. |
| 2011/0160569 A1 | 6/2011 | Cohen et al. |
| 2011/0184241 A1 | 7/2011 | Zubiagte et al. |
| 2011/0196419 A1 | 8/2011 | Cooper |
| 2011/0213346 A1 | 9/2011 | Morley et al. |
| 2011/0230894 A1 | 9/2011 | Simaan et al. |
| 2011/0306929 A1 | 12/2011 | Levesque et al. |
| 2011/0313243 A1 | 12/2011 | Zubiate et al. |
| 2011/0319910 A1 | 12/2011 | Roelle et al. |
| 2012/0067158 A1 | 3/2012 | Kell et al. |
| 2012/0071822 A1 | 3/2012 | Romo et al. |
| 2012/0109274 A1 | 5/2012 | Simaan et al. |
| 2012/0123395 A1 | 5/2012 | Stoy et al. |
| 2012/0241576 A1 | 9/2012 | Yu |
| 2012/0253131 A1 | 10/2012 | Malkowski et al. |
| 2012/0289946 A1 | 11/2012 | Steger |
| 2013/0012928 A1 | 1/2013 | Cooper et al. |
| 2013/0023859 A1 | 1/2013 | Malkowski |
| 2013/0090763 A1 | 4/2013 | Simaan et al. |
| 2013/0096540 A1 | 4/2013 | Cooper et al. |
| 2013/0110131 A1 | 5/2013 | Madhani et al. |
| 2013/0131868 A1 | 5/2013 | Rucker et al. |
| 2013/0165869 A1 | 6/2013 | Blumenkranz et al. |
| 2013/0165945 A9 | 6/2013 | Roelle et al. |
| 2013/0178838 A1 | 7/2013 | Malkowski |
| 2013/0190741 A1 | 7/2013 | Moll et al. |
| 2013/0197539 A1 | 8/2013 | Simaan et al. |
| 2013/0218141 A1 | 8/2013 | Hinman et al. |
| 2013/0231529 A1 | 9/2013 | John et al. |
| 2013/0269109 A1 | 10/2013 | Yu |
| 2013/0274715 A1 | 10/2013 | Chan et al. |
| 2013/0289581 A1 | 10/2013 | Yeung et al. |
| 2013/0300537 A1 | 11/2013 | Bajo et al. |
| 2013/0303945 A1 | 11/2013 | Blumenkranz et al. |
| 2013/0306112 A1 | 11/2013 | Blumenkranz |
| 2013/0338433 A1 | 12/2013 | Goldman et al. |
| 2014/0058406 A1 | 2/2014 | Tsekos |
| 2014/0090506 A1 | 4/2014 | Tobey |
| 2014/0221826 A1 | 8/2014 | Joos et al. |
| 2014/0260755 A1 | 9/2014 | Dong et al. |
| 2014/0316434 A1 | 10/2014 | Simaan et al. |
| 2014/0330432 A1 | 11/2014 | Simann et al. |
| 2015/0073434 A1 | 3/2015 | Simaan et al. |
| 2016/0279789 A1 | 9/2016 | Axinte et al. |
| 2017/0182659 A1 | 6/2017 | Goldman et al. |
| 2018/0257235 A1 | 9/2018 | Alatorre Troncoso et al. |
| 2018/0264643 A1 | 9/2018 | Rabani et al. |
| 2019/0054638 A1 | 2/2019 | Norton et al. |
| 2019/0231449 A1 | 8/2019 | Diolaiti et al. |

FOREIGN PATENT DOCUMENTS

| | | |
|---|---|---|
| CN | 105287000 A | 2/2016 |
| EP | 2335558 | 6/2011 |
| WO | WO2001010292 | 2/2001 |
| WO | WO2005009482 | 2/2005 |
| WO | WO2005112834 | 12/2005 |
| WO | WO2008036304 | 3/2008 |
| WO | WO2009094670 | 7/2009 |
| WO | WO2009097461 | 8/2009 |
| WO | WO2009097539 | 8/2009 |
| WO | WO2009124287 | 10/2009 |
| WO | WO2009140688 | 11/2009 |
| WO | WO2010042611 | 4/2010 |
| WO | WO2011063511 | 6/2011 |
| WO | WO2012015816 | 2/2012 |
| WO | WO2012049623 | 4/2012 |
| WO | WO2013106664 | 7/2013 |
| WO | WO2013043804 | 9/2013 |
| WO | WO2013158974 | 10/2013 |
| WO | WO2013158978 | 10/2013 |
| WO | WO2013158983 | 10/2013 |
| WO | WO2013166293 | 11/2013 |

OTHER PUBLICATIONS

Intellectual Property Office India Examination Report for Application No. 201917026449 dated May 21, 2021 (6 pages including English translation).

European Patent Office Extended Search Report for U.S. Appl. No. 17/879,612 dated Dec. 8, 2020 (6 pages).

Lee et al., "Urgent bedside endoscopy for clinically significant upper gastrointestinal hemorrhage after admission to the intensive care unit", Intensive Care Medicine, 2003 29(10), pp. 1723-1728.

Goldman et al., "Design and performance evaluation of a minimally invasive telerobotic platform for transurethral surveillance and intervention", IEEE Transactions on Biomedical Engineering, vol. 16, No. 4, 2013, pp. 918-925.

O'Brien et al., "3D force control system design for a hydraulic parallel bellows continuum actuator" 2001 IEEE ICRA, May 2001, vol. 3, pp. 2375-2380.

Garbin et al., "Evaluation of a novel disposable upper endoscope for unsedated bedside (non-endoscopy unit based) assessment of the upper gastrointestinal (UGI) tract", Gastrointestinal Endoscopy, vol. 85, No. 5S, 2017.

Stewart et al., "World cancer report 2014," World Health Organization, 2014.

Malik, "Human development report 2013, The Rise of the South: Human Progress in a Diverse World," United Nations Development Programme, UNDP, 2013.

Compare et al., "Screening for and surveillance of gastric cancer," World Journal of Gastroenterology, Oct. 2014, vol. 20, No. 38, pp. 13681-13691.

Shen et al., "Management of gastric cancer in asia: Resource-stratified guidelines," The Lancet Oncology, 2013, vol. 14, No. 12, pp. e535-e547.

(56) References Cited

OTHER PUBLICATIONS

Adami et al., "Primary and secondary prevention in the reduction of cancer morbidity and mortality," European Journal of Cancer, 2001, vol. 37, pp. 118-127.
Patel et al., "Evaluation of a novel flexible snake robot for endoluminal surgery," Surgical Endoscopy, 2015, vol. 29, No. 11, pp. 3349-3355.
Coman et al., "Prospective evaluation of the clinical utility of endoscopic submucosal dissection (esd) in patients with barretts esophagus: A western center experience," Endoscopy International Open, 2016, pp. E715-E721.
Cianchetti et al., "STIFF-FLOP surgical manipulator: Mechanical design and experimental characterization of the single module," IEEE/RSJ International Conference on Intelligent Robots and Systems, 2013, pp. 3576-3581.
Obstein et al., "Sa1665 ultra low-cost endoscopy for gastric cancer screening in low resource settings," Gastrointestinal Endoscopy, vol. 79, No. 5, AB293, 2014.
Stilli et al., "Shrinkable, stiffness-controllable soft manipulator based on a bio-inspired antagonistic actuation principle," IEEE/RSJ International Conference on Intelligent Robots and Systems, 2014, pp. 2476-2481.
Maghooa et al., "Tendon and pressure actuation for a bio-inspired manipulator based on an antagonistic principle," IEEE International Conference on Robotics and Automation, 2015, pp. 2556-2561.
Noh et al., "A three-axial body force sensor for flexible manipulators," IEEE International Conference on Robotics and Automation, 2014, pp. 6388-6393.
Sareh et al., "Bio-inspired tactile sensor sleeve for surgical soft manipulators," IEEE International Conference on Robotics and Automation, 2014, pp. 1454-1459.
Noh et al., "A continuum body force sensor designed for flexible surgical robotics devices," 36th Annual International Conference of the IEEE Engineering in Medicine and Biology Society, 2014, pp. 3711-3714.
Wurdemann et al., "Embedded electro-conductive yarn for shape sensing of soft robotic manipulators," 37th Annual International Conference of the IEEE Engineering in Medicine and Biology Society, 2015, pp. 8026-8029.
Fras et al., "New Stiff-Flop module construction idea for improved actuation and sensing," IEEE International Conference on Robotics and Automation, 2015, pp. 2901-2906.
Gagarina et al., "Modeling and experimental analysis of a new bellow type actuators for active catheter end-effector," Robot and Human Interactive Communication, IEEE, 2001, pp. 612-617.
Bailly et al., "Modeling and control of a hybrid continuum active catheter for aortic aneurysm treatment," Proceedings of the 2005 IEEE International Conference on Robotics and Automation, 2005, pp. 924-929.
Kim et al., "Inchworm-like colonoscopic robot with hollow body and steering device," JSME International Journal Series C Mechanical Systems, Machine Elements and Manufacturing, 2006, vol. 49, No. 1, pp. 205-212.
Iqbal et al., "A guaranteed approach for kinematic analysis of continuum robot based catheter," Robotics and Biomimetics, 2009 IEEE International Conference, pp. 1573-1578.
Falkenhahn et al., "Dynamic modeling of bellows-actuated continuum robots using the euler-lagrange formalism," IEEE Transactions on Robotics, vol. 31, No. 6, 2015, pp. 1483-1496.
Burgner-Kahrs et al., "Continuum robots for medical applications: A survey," IEEE Transactions on Robotics, vol. 31, No. 6, 2015, pp. 1261-1280.
Shiva et al., "Tendonbased stiffening for a pneumatically actuated soft manipulator," IEEE Robotics and Automation Letters, vol. 1, No. 2, 2016, pp. 632-637.
International Search Report and Written Opinion for Related Application No. PCT/US2017/064271 dated Feb. 9, 2018 (7 pages).
Abbott et al., "Haptic virtual fixtures for robot-assisted manipulation," Robotics Research 28, Aug. 2007, 49-64.
Abbott et al., "Stable Forbidden-Region Virtual Fixtures for Bilateral Telemanipulation," vol. 128, No. 1, pp. 53-64, 2006.

Abiko et al., "On-line parameter identification of a payload handled by flexible based manipulator," in 2004 IEEE/RSJ International Conference on Intelligent Robots and Systems (IROS) (IEEE Cat. No. 04CH37566), 2004, vol. 3, pp. 2930-2935.
Adunka et al., "Development and Evaluation of an Improved Cochlear Implant Electrode Design for Electric Acoustic Stimulation," Laryngoscope, 2004, vol. 114, pp. 1237-1241.
Adunka et al., "Preservation of basal inner ear structures in cochlear implantation," Orl J Otorhinolaryngol Relat Spec, 2004, vol. 66, pp. 306-312.
Agarwal et al., "Retinal imaging using a 25-gauge OCT endoprobe through vitreous and vitreous substitutes," in Association for Research in Vision and Ophthalmology (ARVO) Annual Meeting, 2013.
Agrawal et al., "Control of Cable Actuated Devices using Smooth Backlash Inverse," In 2010 IEEE International Conference on Robotics and Automation, Anchorage, AK, 2010, pp. 1074-1079.
Almony et al., "Techniques, rationale, and outcomes of internal limiting membrane peeling," Retina, 2012, 32(5):877-91.
Anderson et al., "Tensor-arm Manipulator Design," ASME J. Mech. Eng., 1967, vol. 89, No. 8, p. 54.
Angeles, "Automatic Computation of the Screw Parameters of Rigid-Body Motions. Part II: Infinitesimally-Separated Positions," Journal of Dynamic Systems, Measurement, and Control 108, Mar. 1986, 32-38.
Anon, "Going Where Others Have Not Gone Before: The Revolutionary Spine Robot Has Now Entered the Very Competitive Spray Painting Market," Industrial Robot, vol. 12, pp. 36-37, 1985.
Anonymous, "Argon laser photocoagulation for macular edema in branch vein occlusion. The Branch Vein Occlusion Study Group," Am J Ophthalmol, 1984, vol. 98, pp. 271-282.
Aoki et al., "Development of Slime Robot Using Bridle Bellows," J. Robot. Mechatron., vol. 16, No. 3, pp. 286-292, 2004.
Aramaki et al., "Tube type micro manipulator using shape memory alloy (SMA)," in Proc. IEEE 6th Int. Symp. Micro Mach. Human Science, Nagoya, Japan, 1995, pp. 115-120.
Asai et al., "Micro-Neurosurgical System in the Deep Surgical Field," in MICCAI 2004 (7th International Conference on Medical Image Computing and Computer-Assisted Intervention), 2004, pp. 33-40.
Ascari et al., "A New Active Microendoscope for Exploring the Sub-arachnoid Space in the Spinal Cord," International Conference on Robotics and Automation, 2003, pp. 2657-2662.
Babbar et al., "Robot-assisted urologic surgery in 2010—Advancements and future outlook," Urol. Ann., 2011, vol. 3, No. 1, pp. 1-7.
Bajo et al., "A Pilot Ex-Vivo Evaluation of a Telerobotic System for Transurethral Intervention and Surveillance," In Hamlyn Symposium on Medical Robotics, 2012.
Bajo et al., "Configuration and Joint Feedback for Enhanced Performance of Multi-Segment Continuum Robots," in IEEE International Conference on Robotics and Automation, 2011, pp. 2905-2912.
Bajo et al., "Constrained Motion Control of Multisegment Continuum Robots for Transurethral Bladder Resection and Surveillance," In Accepted for publication in IEEE International Conference on Robotics and Automation (ICRA'2013).
Bajo et al., "Finding lost wrenches: Using continuum robots for contact detection and estimation of contact location," Robotics and Automation (ICRA), 2010 IEEE International Conference on DOI: 10.1109/ROBOT.2010.5509569; Publication Year: 2010, pp. 3666-3673.
Bajo et al., "Integration and Preliminary Evaluation of an Insertable Robotic Effectors Platform for Single Port Access Surgery," In International Conference on Robotics and Automation (ICRA'2012), pp. 3381-3387.
Bajo et al., "Kinematics-Based Detection and Localization of Contacts Along Multisegment Continuum Robots," IEEE Transactions on Robotics 28,2 (Apr. 2012), 291-302.
Bajo et al., "Robotic-Assisted Micro-Surgery of the Throat: the Trans-Nasal Approach," In Accepted for publication in IEEE International Conference on Robotics and Automation (ICRA'2013).

(56) References Cited

OTHER PUBLICATIONS

Bajo et al., "Robotic-Assisted Micro-Surgery of the Throat: the Trans-Nasal Approach," in IEEE International Conference on Robotics and Automation, 2013, pp. 232-238.
Bajo, "Control, Sensing, and Telemanipulation of Surgical Continuum Robots," Vanderbilt University, 2013, 217 pages.
Baki et al., "Miniature tri-axial force sensor for feedback in minimally invasive surgery," In 2012 4th IEEE RAS & EMBS International Conference on Biomedical Robotics and Biomechatronics (BioRob) (Roma, Italy, Jun. 2012), IEEE, pp. 805-810.
Ballay et al., "Steady-state response audiometry in a group of patients with steeply sloping sensorineural hearing loss," Laryngoscope, 2005, vol. 115, pp. 1243-1246.
Barreto et al., "Automatic camera calibration applied to medical endoscopy," in BMVC 2009—20th British Machine Vision Conference, 2009, pp. 1-10.
Battmer et al., "Evaluation of the neural response telemetry (NRT) capabilities of the nucleus research platform 8: initial results from the NRT trial," Int J Audiol, vol. 43, pp. 10-15, 2004.
Benway et al., "Robot-Assisted Partial Nephrectomy: An International Experience," European Urology, 2010, vol. 57, pp. 815-820.
Bhattacharyya et al., "Characterization of Constraints in Flexible Unknown Environments," In Accepted for publication in IEEE International Conference on Robotics and Automation (ICRA2013).
Bhattacharyya, "Motion Planning and Constraint Exploration for Robotics Surgery," Master Thesis, Vanderbilt University, Nashville, TN. 2011.
Birkfellner et al., "Calibration of tracking systems in a surgical environment," IEEE Transactions on Medical Imaging 17, 5 (Oct. 1998), 737-42.
Bokelberg et al., "Spatial Motion-I: Points of inflection and the differential geometry of screws," Mechanism and Machine Theory 27, 1 (1992), 1-15.
Bookstein, "Principal warps: thin-plate splines and the decomposition of deformations," IEEE Trans. Pattern Anal. Mach. Intell., 1989, vol. 11, 567-585.
Box et al., "Robot-Assisted Notes Nephrectomy: Initial Report," Journal of Endourology, 2008, vol. 22, pp. 503-506.
Box et al., "Robotic radical prostatectomy: long-term outcomes," Current Opinion in Urology, 2008, vol. 18, pp. 173-179.
Braganza et al., "A Neural Network Controller for Continuum Robots," IEEE Trans. Robot., 2007, vol. 23, No. 6, pp. 1270-1277.
Brandt et al., "A Compact Robot for Image Guided Orthopedic Surgery: Concept and preliminary Results," in Lecture Notes in Computer Science (LNCS) vol. 1205, J. Troccaz, E. Grimson, and R. Mosges, Eds.: Springer, 1997, 767-776.
Brandt et al., "CRIGOS: A compact robot for image-guided orthopedic surgery," IEEE Transactions on Information Technology in Biomedicine, 1999, vol. 3, pp. 252-260.
Brown et al., "A novel GJB2 (connexin 26) mutation, F142L, in a patient with unusual mucocutaneous findings and deafness," J Invest Dermatol, 2003, vol. 121, pp. 1221-1223.
Burgner et al., "A Bimanual Teleoperated System for Endonasal Skull Base Surgery," In 2011 IEEE International Conference on Intelligent Robots and Systems (San Francisco, CA, Sep. 2011), IEEE, pp. 2517-2523.
Burgner et al., "A Telerobotic system for transnasal surgery," IEEE/ASME Transactions on Mechatronics, 2014, vol. 19, No. 3, pp. 996-1006.
Buss et al., "Selectively Damped Least Squares For Inverse Kinematics," 2005, vol. 10, No. 3, pp. 37-49.
Cahill et al., "The effect of arteriovenous sheathotomy on cystoid macular oedema secondary to branch retinal vein occlusion," Br J Ophthalmol, 2003, vol. 87, pp. 1329-1332.
Cahill et al., "Intraperitoneal virtual biopsy by fibered optical coherence tomography (OCT) at natural orifice transluminal endoscopic surgery (Notes)," J. Gastrointest. Surg., 2010, vol. 14, No. 4, pp. 732-738.
Camarillo et al., "Configuration Tracking for Continuum Manipulators with Coupled Tendon Drive," IEEE Transactions on Robotics 25, 4 (Aug. 2009), 798-808.
Camarillo et al., "Mechanics Modeling of Tendon-Driven Continuum Manipulators," IEEE Transaction on Robotics 24,6 (2008), 1262-1273.
Camarillo et al., "Vision based 3-D shape sensing of flexible manipulators," In 2008 IEEE International Conference on Robotics and Automation (Pasadena, CA, 2008), pp. 2940-2947.
Cannon et al., "Port Placement Planning in Robot-Assisted Coronary Attery Bypass," IEEE Transactions on Robotics and Automation, 2003, vol. 19, pp. 912-917.
Carpentier et al., "Residual internal limiting membrane after epiretinal membrane peeling: results of the Pan-American Collaborative Retina Study Group," Retina, 2013, pp. 2026-2031.
Cassilly et al., "Optimizing motion scaling and magnification in robotic surgery," Surgery, 2004, vol. 136, No. 2, pp. 291-294.
Cauberg et al., "How to improve the effectiveness of transurethral resection in nonmuscle invasive bladder cancer?" Current Opinion in Urology 2 19, 5 (2009), 504-510.
Cavusoglu et al., "Robotics for Telesurgery: Second Generation Berkley/UCSF Laprascopic Telesurgical Workstation and Looking towards the Future Applications," in 39th Allerton Conference on Communication, Control and Computing Monticello, Italy, 2001.
Chan et al., "A Weighted Least-Norm Solution Based Scheme for Avoiding Joint Limits for Redundant Joint Manipulators," IEEE Transaction on Robotics and Automation 11,2 (1995), 286-292.
Chang et al., "LIBSVM: A Library for Support Vector Machines," 2001. [Online]. Available: http://www.csie.ntu.edu.tw/cjlin/libsvm.
Chatzilias et al., "Robotic control in hand-assisted laparoscopic nephrectomy in humans—A pilot study," in Conference Proceedings—26th Annual International Conference of the IEEE Engineering in Medicine and Biology Society, EMBC 2004, Sep. 1, 2004-Sep. 5, 2004, San Francisco, CA, United states, 2004, pp. 2742-2745.
Chen et al., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.
Chen et al., "Evaluation of trajectories and contact pressures for the straight nucleus cochlear implant electrode array—a two dimensional application of finite element analysis," Medical Engineering & Physics, 2003, vol. 25, pp. 141-147.
Chen et al., "Identification of the Flexible Actuator of a Clonoscope," IEEE/RSJ International Conference on Intelligent Robots and Systems, 2003, pp. 3355-3360.
Chen et al., "Linkage of otosclerosis to a third locus (OTSC3) on human chromosome 6p21.3-22.3," J Med Genet, 2002, vol. 39, pp. 473-477.
Chen et al., "Sensor-based guidance control of a continuum robot for a semi-autonomous colonoscopy," Robot. Autonom. Syst., 2009, vol. 57, No. 6-7, pp. 712-722.
Chen et al., "Treatment of fingertip degloving injury using the bilaterally innervated sensory cross-finger flap," Ann. Plast. Surg. ,2014, vol. 73, pp. 645-651.
Cheung et al., "Minimally invasive cystectomy approaches in the treatment of bladder cancer," Expert Rev. Anticancer Ther., 2012, vol. 12, No. 6, pp. 733-741.
Chiaverini et al., "Review of the damped least-squares inverse kinematics with experiments on an industrial robot manipulator," IEEE Trans. Control Syst. Technol., 1994, vol. 2, No. 2, pp. 123-134.
Chirikjian et al., "A Geometric Approach to Hyper-Redundant Manipulator Obstacle Avoidance," ASME Journal of Mechanical Design, 1992, vol. vol. 114, pp. 580-585.
Chirikjian et al., "A Hyper-Redundant Manipulator," IEEE Robotics and Automation Magazine, pp. pp. 22-29, 1994.
Chirikjian et al., "A Modal Approach to Hyper-Redundant Manipulator Kinematics," IEEE Transactions on Robotics and Automation, vol. 10, pp. 343-354, 1994.
Chirikjian et al., "An obstacle avoidance algorithm for hyper-redundant manipulators," In Proceedings, IEEE International Conference on Robotics and Automation (1990), IEEE Comput. Soc. Press, pp. 625-631.

(56) References Cited

OTHER PUBLICATIONS

Chirikjian et al., "Design and Experiments with a 30 DOF Robot," IEEE International Conference on Robotics and Automation, 1993, pp. 113-119.

Chirikjian et al., "Kinematically Optimal Hyper-Redundant Manipulator Configurations," IEEE Transactions on Robotics and Automation, 1995, vol. 11, pp. 794-806.

Chirikjian, "General Methods for Computing Hyper-Redundant Manipulator Inverse Kinematics," IEEE/RSJ International conference on Intelligent Robots and Systems (IROS), 1993, pp. 1067-1073.

Cho et al., "Macro-micro manipulation with visual tracking and its application to wheel assembly," Int. J. Control. Autom. Syst., 2005, vol. 3, No. 3, pp. 461-468.

Chung et al., "Arteriovenous crossing sheathotomy versus intravitreal triamcinolone acetonide injection for treatment of macular edema associated with branch retinal vein occlusion," Graefes Arch Clin Exp Ophthalmol, 2008, vol. 246, pp. 967-974.

Cohen et al., "Improved and Simplified Methods for Specifying Positions of the Electrode bands of a Cochlear Implant Array," The American Journal of Otology, 1996, vol. 17, pp. 859-865.

Cohen et al., "Surgical technique for the Nucleus Contour cochlear implant," Ear Hear, 2002, vol. 23, pp. 59S-66S.

Conrad et al., "Robotic Calibration Issues: Accuracy, Repeatability and Calibration," in 8th Mediterranean Conference on Control & Automation, 2000, pp. 17-19.

Coscas et al., "Management of retinal vein occlusion—consensus document," 11 Ophthalmologica, 2011, vol. 226, pp. 4-28.

Creighton et al., "Safe Superconducting Current Discharge for the Magnetic Stereotaxis System," IEEE Transactions on Magnetics, 1999. vol. 35, pp. 4285-4290.

Croom et al., "Visual Sensing of Continuum Robot Shape Using Self-Organizing Maps," in 2010 IEEE International Conference on Robotics and Automation (Anchorage, AK, 2010), pp. 4591-4596.

Dahiya et al., "Tactile Sensing From Humans to Humanoids," IEEE Trans. Robot., 2010, vol. 26, No. 1, pp. 1-20.

Dandurand, "The Rigidity of Compound Spatial Grid," Structural Topology, 1984, vol. 10, pp. 41-56.

Dario et al., "A Miniature Steerable End-Effector for Application In an Integrated System for Computer-Assisted Arthroscopy," IEEE International Conference on Robotics and Automation, 1997, pp. 1573-1579.

Dario et al., "Development and In Vitro Testing of a Miniature Robotic System for Comuter-Assisted Clonoscopy," 1999, vol. 4, pp. 1-14.

Dario et al., "Robotics as a future and emerging technology: Biomimetics, cybernetics, and neuro-robotics in European projects," IEEE Robotics and Automation Magazine, 2005, vol. 12, pp. 29-45.

Dasgupta et al., "The Stewart Platforms Manipulator: A Review," In Mechanism and Machine Theory, 2000, vol. 35, pp. 15-40.

D'Attansio et al., "A Semi-Automatic Handheld Mechatronic Endoscope with Collision-Avoidance Capabilities," IEEE International Conference on Robotics & Automation, 2000, pp. 1586-1591.

Davies et al., "Robotic control in knee joint replacement surgery," Proceedings of the Institution of Mechanical Engineers, Part H: Journal of Engineering in Medicine, 2007, vol. 221, pp. 71-80.

De Luca et al., "Collision Detection and Safe Reaction with the DLR-III Lightweight Manipulator Arm," In 2006 IEEE/RSJ International Conference on Intelligent Robots and Systems (Beijing, China, 2006), pp. 1623-1630.

De Luca et al., "Modeling of Robots in Contact with a Dynamic Environment," IEEE Transaction on Robotics and Automation 10,4 (1994), 542-548.

Debus et al., "Contact State Estimation using Multiple Model Estimation and Hidden Markov Models," The International Journal of Robotics Research 23, 4-5 (2004), 399-413.

Degani et al., "Highly Articulated Robotic Probe for Minimally Invasive Surgery," In 2006 IEEE International Conference on Robotics and Automation (Orlando, FL, USA, 2006), pp. 4167-4172.

Deklaj et al., "Laparoscopic radical versus laparoscopic partial nephrectomy for clinical T1bN0M0 renal tumors: comparison of perioperative, pathological, and functional outcomes," Journal of endourology / Endourological Society, 2010, vol. 24, pp. 1603-1607.

Del Giudice et al., "Design considerations for continuum robot actuation units enabling dexterous transurethral bladder cancer resection," in ASME 2016 International Design Engineering Technical Conferences and Computers and Information in Engineering Conference. American Society of Mechanical Engineers, 2016, pp. V05AT07A030-1-V05AT07A030-10.

Della Santa et al., "Steerable Microcatheters Actuated by Embedded Conducting Polymer Structures," Journal of Intelligent Material Systems and Structures, 1996, vol. 7, pp. 292-300.

Deo et al., "Robot subtask performance with singularity robustness using optimal damped least-squares," in Proceedings 1992 IEEE International Conference on Robotics and Automation, 1993, pp. 434-441.

Dhingra et al., A Gröbner-Sylvester Hybrid Method for Closed-Form Displacement Analysis of Mechanisms, ASME Journal of Mechanical Design, 2000, vol. 122, pp. 431-438.

Dietmaier, The Stewart-Gough Platform of General Geometry Can Have 40 Real Postures, in Advances in Robot Kinematics—Analysis and Control (ARK-1998): Kluwer Academic Publishers, 1998, pp. 7-16.

Dimaio, "da Vinci and Beyond," In 2010 IEEE International Conference on Robotics and Automation Workshop on Medical Cyber-Physical Systems (Anchorage, AK, 2010).

Ding et al., "Design and Coordination Kinematics of an Insertable Robotic Effectors Platform for Single-Port Access Surgery," IEEE/ASME Transactions on Mechatronics (2012), 1-13.

Ding et al., "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.

Dogangil et al., "A review of medical robotics for minimally invasive soft tissue surgery," Proceedings of the Institution of Mechanical Engineers, Part H: Journal of Engineering in Medicine, 2010, vol. 224, pp. 653-679.

Dupont et al., Design and Control of Concentric-Tube Robots, IEEE Transaction on Robotics 26, 2 (2010), 209-225.

Eberman et al., "Determination of Manipulator Contact Information from Joint Torque Measurements," In Experimental Robotics I, vol. 139. Springer, 1990, pp. 463-473.

Ebert-Uphoff et al., "Inverse Kinematics of Discretely Actuated Hyper-Redundant Manipulators Using Workspace Densities," IEEE Int. Conf. on Robotics and Automation, 1996, pp. 139-145.

Egeland, "Task-space tracking with redundant manipulators," IEEE J. Robot. Autom., 1987, vol. 3, No. 5, pp. 471-475.

Entsfellner et al., "Micro-Macro Telemanipulator for Middle-Ear Microsurgery," in Robotics; Proceedings of ROBOTIK 2012; 7th German Conference on, 2012, pp. 395-398.

Eshraghi et al., "Comparative Study of Cochlear Damage with Three Perimodiolar Electrode Designs," The Laryngeoscope, 2003, vol. 113, pp. 415-419.

Fadda et al., "Computer Assisted Planning for Total Knee Arthoplasty," in Lecture Notes in Computer Science (LNCS) vol. 1205, J. Troccaz, E. Grimson, and R. Mosges, Eds.: Springer, 1997, 619-628.

Farah et al., "Dyes in ocular surgery: principles for use in chromovitrectomy," Am J Ophthalmol, 2009, vol. 148, pp. 332-340.

Faugere et al., "Combinatorial Classes of Parallel Manipulators," Mechanism and Machine Theory, 1995, vol. 6, pp. 765-776.

Featherstone et al., "A General Contact Model for Dynamically-Decoupled Force/Motion Control," In 1999 IEEE International Conference on Robotics and Automation (1999), no. May, pp. 3281-3286.

(56) References Cited

OTHER PUBLICATIONS

Featherstone, "Modeling and Control of Contact Between Constrained Rigid Bodies," IEEE Transaction on Robotics and Automation 20, 1 (2004), 82-92.

Ficarra et al., "Evidence from robot-assisted laparoscopic radical prostatectomy: a systematic review," Eur. Urol., 2007, vol. 51, No. 1, discussion 56, pp. 45-56.

Fichter, "A Stewart Platform-Based Manipulator: General Theory and Practical Construction," Int. J. Robotics Research, 1986, vol. 5, pp. 157-182.

Fine et al., "A novel dual-arm dexterous ophthalmic microsurgical robot: applications for retinal vascular cannulation and stent deployment," In American Society of Retinal Specialists, Retina congress 2009, New York, NY, Sep. 4-Oct. 4.

Fine et al., "Could Robots Ever Do Retina Surgery?" Review of Ophthalmology, vol. 17, No. 5, Issue: May 1, 2010.

Fishman et al., "Flouroscopically Assisted Cochlear Implantation," Otology & Neurotology, 2003, vol. 24, pp. 882-886.

Fitts, "The information capacity of the human motor system in controlling the amplitude of movement," J. Exp. Psychol., 1954, vol. 47, No. 6, p. 381-391.

Frangieh et al., "Histopathologic study of nine branch retinal vein occlusions," Arch Ophthalmol., 1982, vol. 100, pp. 1132-1140.

Freschi et al., "Technical review of the da Vinci surgical telemanipulator," Int. J. Med. Robot., 2013, 9: 396-406.

Fritzsche et al., "Resectoscope with an easy to use twist mechanism for improved handling," Current Directions in Biomedical Engineering, 2016, 2(1):379-382.

Gantz et al., "Preservation of hearing in cochlear implant surgery: advantages of combined electrical and acoustical speech processing," Laryngoscope, 2005, vol. 115, pp. 796-802.

Gaponov et al., Twisted string actuation systems: A study of the mathematical model and a comparison of twisted strings. IEEE/ASME Transactions on Mechatronics, 19(4), pp. 1331-1342.

Garbin et al., "Design of a Disposable Endoscope with Intrinsic Pneumatic Actuation," 2017, Hamlyn Symposium, London, Jun. 25-28.

Garbin et al., "Evaluation of a novel disposable upper endoscope for unsedated bedside (non-endoscopy unit based) assessment of the upper gastrointestinal (UGI) tract," DDW 2017, May 6-9, Gastrointestinal Endoscopy, 2017, vol. 85, No. 5S, Su1180.

Garbin et al., "Toward a low-cost soft robotic manipulator based on fluid-actuated bellows for gastric cancer screening," 2017, Hamlyn Symposium London, Jun. 25-28, 2017, 8 pages.

Garty et al., "Development of an ultrahigh-throughput robotically-based biodosimetry workstation using in-situ assays," In 13th International Congress of Radiation Research, San Francisco, California, Jul. 8-12, 2007.

Gharib, "A new design for variable diameter orifice mechanism," in ASME 2012 International Mechanical Engineering Congress and Exposition. American Society of Mechanical Engineers, 2012, pp. 1551-1552.

Ghazvini, "Reducing the Inverse Kinematics of Manipulators to the Solution of a Generalized Eigenproblem," in Computational Kinematics: Kluwer Academic Publishers, 1993, pp. 15-26.

Godage et al., "Shape Function-Based Kinematics and Dynamics for Variable Length Continuum Robotic Arms," 2011 IEEE International Conference on Robotics and Automation (May 9-13, 2011).

Goldman et al., "Algorithms for Autonomous Exploration and Estimation in Compliant Environments," Robotica, 31(1), 71-88, 2013.

Goldman et al., "Compliant Motion Control for Continuum Robots with Intrinsic Actuation Sensing," in IEEE International Conference on Robotics and Automation, 2011, pp. 1126-1132.

Goldman et al., "Compliant Motion Control for Multi-segment Continuum Robots With Actuation Force Sensing," IEEE Transaction on Robotics, 2014, vol. 30, No. 4, pp. 890-902.

Goldman et al., "Rapidly Deployable Telerobotic Slave for Transurethral Exploration and Intervention," In presented in the 2011 Annual Engineering and Urology Society annual meeting, May 14, 2011, Washington, DC.

Goldman, "Analysis, Algorithms, and Control for Intelligent Surgical Exploration and Intervention," Phd Thesis, Columbia University (graduated with distinction) 2011.

Gong et al., "Four-arm robotic partial nephrectomy for complex renal cell carcinoma," World journal of urology, 2010, vol. 28, pp. 111-115.

Gosselin et al., "Singularity Analysis of Closed-Loop Kinematic Chains," IEEE Transactions on Robotics and Automation, 1990, vol. 6, pp. 281-290.

Gough et al., "Universal Tyre Test Machine," Proceedings, Ninth International Technical Congress F.I.S.I.T.A., 1962, pp. 117-137.

Grace, "Kinematic Design of an Opthalmic Surgery Robot and Feature Extracting Bilateral Manipulation," in Mechanical Engineering: Northwestern University, 1995, Dissertation, 95 pages.

Gravagne et al., "Good Vibrations: A Vibration Damping Setpoint Controller for Continuum Robots," Proceedings of the 2001 IEEE International Conference on Robotics & Automation (May 21-26, 2001).

Gravagne et al., "Kinematic Transformations for Remotely-Actuated Planar Continuum Robots," In 2000 IEEE International Conference on Robotics & Automation (San Francisco, 2000), No. April, pp. 19-26.

Gravagne et al., "Manipulability, Force, and Compliance Analysis for Planar Continuum Manipulators," IEEE Transactions on Robotics and Automation, vol. 18, No. 3 (Jun. 2002).

Gravagne et al., "Large deflection dynamics and control for planar continuum robots," IEEE/ASME Trans. Mechatronics, 2003, vol. 8, No. 2, pp. 299-307.

Gstoettner et al., "Hearing preservation In cochlear implantation for electric acoustic stimulation," Acta Otolaryngol, 2004, vol. 124, pp. 348-352.

Guo et al., "Micro Active Guide Wire Catheter System—Characteristic Evaluation, Electrical Model and Operability Evaluation of Micro Active Catheter," IEEE International Conference on Robotics and Automation (ICRA'96), 1996, pp. 2226-2231.

Guo et al., "Micro Active Guide Wire Catheter System—Characteristic Evaluation, Electrical Model and Operability Evaluation of Micro Active Catheter," Sixth Int'l Symposium on Micro Machine and Human Science (MHS'95), 1995, pp. 131-136.

Guo et al., "Micro Active Guide Wire Catheter System," IEEE International Conference on Robotics and Automation, 1995, pp. 172-177.

Guo et al., "Micro Catheter System with Active Guide Wire—Structure, Experimental Results and Characteristic Evaluation of Active Guide Wire Catheter Using ICPF Actuator," Proc. 5th Int'l Symp. on Micro Machine and Human Science (MHS'94), 1994, pp. 191-197.

Gupta et al., "Current and evolving uses of optical coherence tomography in the genitourinary tract," Curr. Urol. Rep., 2015, 16:15, 7 pages.

Guthart et al., "The IntuitiveTM Telesurgery System: Overview and Application," In 2000 IEEE International Conference on Robotics and Automation (2000), pp. 618-621.

Haber et al., "Novel robotic da Vinci instruments for laparoendoscopic single-site surgery," Urology, 2010, vol. 76, pp. 1279-1282.

Haddadin et al., Collision Detection and Reaction: A Contribution to Safe Physical Human-Robot Interaction. In 2008 IEEE/RSJ International Conference on Intelligent Robots and Systems (Nice, France, 2008), pp. 3356-3363.

Haga et al., "Small Diameter Active Catheter Using Shape Memory Alloys," Proc. of IEEE Micro Electro Mechanical Systems, 1998, pp. 419-424.

Hale, "Medical Applications of magnet Devices," IEEE Transactions on Magnetics, 1975, vol. 11, pp. 1405-1407.

Hamid et al., "Design and Synthesis of Wire-Actuated Universal-Joint Wrists for Surgical Application," In 2009 IEEE International Conference on Robotics and Automation, pp. 1807-1831. Kobe, Japan.

(56) References Cited

OTHER PUBLICATIONS

Hannan et al., "Analysis and initial experiments for a novel elephant's trunk robot," IEEE/RSJ International Conference on Intelligent Robots and Systems (IROS 2000), 2000, pp. 330-337.

Hannan et al., "Kinematics and the Implementation of an Elephant's Trunk Manipulator and Other Continuum Style Robots," Journal of Robotic Systems 20, 2 (2003), 45-63.

Hannan et al., "The 'elephant trunk' manipulator, design and implementation," proceedings of IEEE/ASME International conference on Advanced Intelligent Mechatronics, 2001, vol. 1, pp. 14-19.

Haritoglou et al., "Five-year follow-up of macular hole surgery with peeling of the internal limiting membrane: update of a prospective study," Retina, 2006, vol. 26(6), pp. 618-622.

Harris et al., "Experiences with Robotic Systems for Knee Surgery," vol. 1205, J. Troccaz, E. Grimson, and R. Mosges, Eds. Springer, 1997, pp. 757-766.

Hassan et al., "Active-braid, a bioinspired continuum manipulator," IEEE Robotics and Automation Letters, 2017, vol. 2, No. 4, pp. 2104-2110.

Hayward, "Fast Collision Detection Scheme by Recursive Decomposition of A Manipulator Workspace," Proceedings IEEE International Conference on Robotics and Automation, vol. 3 (1986).

Heimann et al., "Primary vitrectomy for rhegmatogenous retinal detachment: an analysis of 512 cases," Graefes Arch Clin Exp Ophthalmol., 2006, vol. 244, pp. 69-78.

Hendrick et al., "A multi-arm hand-held robotic system for transurethral laser Prostate surgery," in 2014 IEEE International Conference on Robotics and Automation (ICRA), 2014, pp. 2850-2855.

Henrich et al., "Quantification of Contrast Recognizability During Brilliant Blue G (BBG) and Indocyanine Green (ICG) Assisted Chromovitrectomy," Invest Ophthalmol Vis Sci., 2011, 52(7): 4345-4349.

Herrell et al., "Toward Image-Guided Robotic Surgery: System Validation," J Urol. Feb. 2009; 181(2): 783-9 Discussion 789-90. Epub Dec. 16, 2008.

Hillel et al., "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008. 01.021, Aug. 2008.

Hirai et al., "Modeling of Deformable Thin Parts for their Manipulation," IEEE International Conference on Robotics and Automation, 1994, pp. 2955-2960.

Hirai et al., "Towards a Task Planning for Deformable object Manipulation—Formulation and Computation of Linear Object Deformation," IEEE International Conference on Robotics and Automation, 1995, pp. 80-85.

Hirose et al., "Coupled Tendon-Driven Multijoint Manipulator," IEEE Int. Conf. Robotics & Automation, 1991, pp. 1268-1275.

Hirose et al., "The Development of Soft Gripper for the Versatile Robot Hand," Mechanism and Machine Theory, 1987, vol. 13, pp. 351-359.

Hirose et al., "Tensor Actuated Elastic Manipulator," in Proceedings of the Sixth World Congress on Theory of Machines and Mechanisms, 1983, pp. 978-981.

Ho et al., "Robot Assisted Knee Surgery," IEEE Engineering in Medicine and Biology Magazine 14, 3 (1995), 292-299.

Hockstein et al., "Robotic microlaryngeal surgery: a technical feasibility study using the daVinci surgical robot and an airway mannequin," The Laryngoscope, 2005, vol. 115, No. 5, pp. 780-785.

Hodac et al., "Decoupled macro/micro-manipulator for fast and precise assembly operations: design and experiments," in Proc. SPIE 3834, Microrobotics and Microassembly, 1999, pp. 122-130.

Hodges et al., "Conservation of residual hearing with cochlear implantation," Am J Otol, 1997, vol. 18, pp. 179-183.

Hogan, "Impedance Control: An Approach to Manipulation: Part I Theory," Journal of Dynamic Systems, Measurement, and Control 107, 1 (1985), 1.

Hongo et al., "NeuRobot: Telecontrolled Micromanipulator System for Minimally Invasive Microneurosurgery—Preliminary Results," Neurosurgery, 2002, vol. 51, pp. 985-988.

Howell, "Compliant Mechanisms," Wiley-Interscience, 2001.

Hunt, "Structural Kinematics of In-Parallel-Actuated Robot arms," Journal of Mechanisms, Transmissions, and Automation in Design, 1983, vol. 105, pp. 705-712.

Husty, "An Algorithm for Solving the Direct Kinematics of General Stewart-Gough Platforms," Mechanism and Machine Theory, 1996, vol. 31, pp. 365-380.

Huttenbrink et al., "Movements of Cochlear Implant Electrodes Inside the Cochlea during Insertion: An X-ray Microscopy Study," Otology & Neurotology, 2002, vol. 23, pp. 187-191.

Hwang et al., "Combined arteriovenous sheathotomy and intraoperative intravitreal triamcinolone acetonide for branch retinal vein occlusion," Br J Ophthalmol, 2010, vol. 94, pp. 1483-1489.

Hyun-Soo Yoon et al., "A 4-DOF flexible continuum robot using a spring backbone," in Proc. IEEE Int. Conf. Mechatron. Autom., Changchun, China, 2009, pp. 1249-1254.

Ikits et al., "An Improved Calibration Framework for Electromagnetic Tracking Devices," In 2001 IEEE Virtual Reality (Yokohama, Japan, 2001), IEEE Comput. Soc, pp. 63-70.

Ikuta et al. "Development of remote micro-surgery robot and new surgical procedure for Jeep and narrow space," In 2003 IEEE International Conference on Robotics and Automation (Taipei, Taiwan, 2003), vol. 1, IEEE, pp. 1103-1108.

Ikuta et al., "Multi-degree of freedom hydraulic pressure driven safety active catheter," in Proc. IEEE Int. Conf. Robot. Autom., Orlando, FL, 2006, pp. 4161-4166.

Ikuta et al., "Remote Microsurgery System for Deep and Narrow Space Development of New Surgical Procedure and Micro-robotic Tool Sophisticated Medical Treatment and Cases," in Medical Image Computing and Computer-Assisted Intervention, Tokyo, Japan, 2002, pp. 163-172.

Immega et al., "The KSI Tentacle Manipulator," IEEE Int. Conf. on Robotics and Automation, 1995, pp. 3149-3154.

Innocenti, "Forward Kinematics in Polynomial Form of the General Stewart Platform," ASME J. of Mechanical Design, 2001, vol. 123, pp. 254-260.

International Search Report and Written Opinion for Application No. PCT/US2017/064271 dated Feb. 9, 2018 (7 pages).

International Search Report and Written Opinion for Application No. PCT/US2018/050948 dated Nov. 20, 2018 (8 pages).

International Search Report and Written Opinion for PCT Application No. PCT/US2013/021167 dated Mar. 22, 2013.

International Search Report and Written Opinion for PCT Application No. PCT/US2013/037336 dated Jul. 25, 2013.

International Search Report and Written Opinion for PCT Application No. PCT/US2013/037346 dated Aug. 27, 2013.

International Search Report and Written Opinion for PCT Application No. PCT/US2013/037353 dated Aug. 19, 2013.

International Search Report and Written Opinion for PCT Application No. PCT/US2013/039280 dated Aug. 20, 2013.

Ishiyama et al., "Magnetic micromachines for medical applications," Journal of Magnetism and Magnetic Materials, 2002, vol. 242-245, pp. 41-46.

Ivanescu et al., "A variable structure controller for a tentacle manipulator," in Proceedings of 1995 IEEE International Conference on Robotics and Automation, 1995, vol. 3, pp. 3155-3160.

Iyer et al., "An eye model for practicing vitreoretinal membrane peeling," Arch. Ophthalmol., 2006, vol. 124, No. 1, pp. 108-110.

James et al., "Preservation of residual hearing with cochlear implantation: how and why," Acta Otolaryngol, 2005, vol. 125, pp. 481-491.

Jayender et al., "Robot-assisted Active Catheter Insertion: Algorithms and Experiments," Int. J. Robot. Res., 2009, vol. 28, No. 9, pp. 1101-1117.

Jazayeri et al., "Distal digital replantation," Plast. Reconstr. Surg., 2013, vol. 132, No. 5, pp. 1207-1217.

Jensen et al., "Toward robot-assisted vascular microsurgery in the retina," Graefes Arch Clin Exp Ophthalmol, 1997, vol. 235, pp. 696-701.

Jerjes et al., "In vitro examination of suspicious oral lesions using optical coherence tomography.," Br. J. Oral Maxillofac. Surg., 2010, vol. 48, No. 1, pp. 18-25.

(56) References Cited

OTHER PUBLICATIONS

Jones et al., "A New Approach to Jacobian Formulation for a Class of Multi-Section Continuum Robots," in IEEE International Conference on Robotics and Automation, 2005, pp. 3268-3273.
Jones et al., "Practical Kinematics for Real-Time Implementation of Continuum Robots," IEEE Trans. Robot., 2006, vol. 22, No. 6, pp. 1087-1099.
Jones, "Kinematics for Multisection Continuum Robots," IEEE Transactions on Robotics, vol. 22, No. 1 (Feb. 2006), 43-57.
Joos et al., "A miniature forward-imaging optical coherence tomography probe," in Proc. SPIE 8209, Ophthalmic Technologies XXII, 82090Z, 2012, p. 82090Z-82090Z-7.
Joos et al., "Miniature real-time intraoperative forward-imaging optical coherence tomography probe," Biomed. Opt. Express, 2013, vol. 4, No. 8, pp. 1342-1350.
Joos et al., "Preliminary Design and Evaluation of a B-Scan OCT-Guided Needle," Photonics, 2014, vol. 1, No. 3, pp. 260-266.
Kanazawa et al., "Current reconstructive techniques following head and neck cancer resection using microvascular surgery," Ann. Vasc. Dis., 2011, vol. 4, No. 3, pp. 189-195.
Kaouk et al., "Robotic assisted laparoscopic sural nerve grafting during radical prostatectomy: initial experience," J. Urol., 2003, vol. 170, No. 3, pp. 909-912.
Kapadia et al., "Empirical investigation of closed-loop control of extensible continuum manipulators," in 2014 IEEE/RSJ International Conference on Intelligent Robots and Systems, 2014, pp. 329-335.
Kapoor et al., "A Constrained Optimization Approach to Virtual Fixtures for Multi-Handed Tasks," In IEEE International Conference on Robotics and Automation (Pasadena, CA, 2008), pp. 3401-3406.
Kapoor et al., "A System for Speed and Torque Control of DC Motors with Application to Small Snake Robots," 2004.
Kapoor et al., "Constrained control for surgical assistant robots," in IEEE International Conference on Robotics and Automation, 2006, pp. 231-236.
Kapoor et al., "Spatial Motion Constraints for Robot Assisted Suturing using Virtual Fixtures," 2005, vol. 3750, pp. 89-96.
Kapoor et al., "Suturing in Confined Spaces: Constrained Motion Control of a Hybrid 8-DoF Robot", in IEEE Conference on Advanced Robotics, 2005, pp. 452-459.
Kapoor et al., "Telemanipulation of Snake-Like Robots for Minimally Invasive Surgery of the Upper Airway," in MICCAI 2006 workshop on medical robotics, Copenhagen, 2006.
Karger, "Architecture Singular Parallel Manipulators," in Advances In Robot Kinematics: Analysis and Control: Kluwer Academic Publishers, 1998, pp. 445-454.
Kaul et al., "da Vinci-assisted robotic partial nephrectomy: technique and results at a mean of 15 months of follow-up," European urology, 2007, vol. 51, discussion 191-2, pp. 186-191.
Kayalar et al., "Clinical applications of free arterialized venous flaps," J. Plast. Reconstr. Aesthet. Surg., 2014, vol. 67, No. 11, pp. 1548-1556.
Kazanzides et al., "An Integrated System for Cementless Hip Replacement," IEEE Engineering in Medicine and Biology, 1995, vol. 14, pp. 307-313.
Kelly, "Vitreous surgery for idiopathic macular holes: results of a pilot study," Arch Ophthalmol, 1991, vol. 109, pp. 654-659.
Kernt et al., "Indocyanine green increases light-induced oxidative stress, senescence, and matrix metalloproteinases I and 3 in human RPE cells," Acta Ophthalmol, 2012, 90: 571-579.
Kesner et al., "Design and Control of Motion Compensation Cardiac Catheters," In 2010 IEEE International Conference on Robotics and Automation (Anchorage, AK, 2010), pp. 1059-1065.
Kesner et al., "Force Control of Flexible Catheter Robots for Beating Heart Surgery," In 2011 IEEE International Conference on Robotics and Automation (Shanghai, China, Jan. 2011), pp. 1589-1594.
Kesner et al., "Position Control of Motion Compensation Cardiac Catheters," IEEE Transaction on Robotics 27, 6 (2011), 1045-1055.
Ketten et al., "In vivo measures of cochlear length and insertion depth of Nucleus cochlear implant electrode arrays," Ann. Otol. Rhinol. Laryngol., 1998, vol. 107, pp. 1-17.
Kha et al., "Stiffness properties for Nucleus standard straight and contour electrode arrays," Medical Engineering & Physics, 2004, vol. 26, pp. 677-685.
Khatib, "A Unified Approach for Motion and Force Control of Robot Manipulators: The Operational Space Formulation," IEEE Journal of Robotics and Automation 3,1 (1987), 43-53.
Kiefer et al., "Conservation of low-frequency hearing in cochlear implantation," Acta Otolaryngol, 2004, vol. 124, pp. 272-280.
Kienzle et al., "Total Knee Replacement," IEEE Engineering in Medicine and Biology, 1995, vol. 14, pp. 301-306.
Kim et al., "A physically-based haptic rendering for telemanipulation with visual information: Macro and micro applications," in 2008 IEEE/RSJ International Conference on Intelligent Robots and Systems, 2008, pp. 3489-3494.
Knight et al., "Computer-assisted, robot-enhanced open microsurgery in an animal model," J. Laparoendosc. Adv. Surg. Tech. A, 2005, vol. 15, No. 2, pp. 182-185.
Kragic et al., "Human-Machine Collaborative Systems for Microsurgical Applications," The International Journal of Robotics Research 24, 9 (Sep. 2005), 731-741.
Kutz et al., "Neuropsychological testing in the screening for cochlear implant candidacy," Laryngoscope, 2003, vol. 113, pp. 763-766.
Kwartowitz et al., "Toward image-guided robotic surgery: determining intrinsic accuracy of the da Vinci robot," Int. J. Comput. Assist. Radiol. Surg., 2006, vol. 1, No. 3, pp. 157-165.
Kwartowitz et al., "Update: Toward image-guided robotic surgery: determining the intrinsic accuracy of the daVinci-S robot," Int. J. Comput. Assist. Radiol. Surg., 2007, vol. 1, No. 5, pp. 301-304.
Kwartowitz, "Towards Image Guided Robotic Surgery: Multi-Arm Tracking Through Hybrid Localization," Int J Comput Assist Radiol Surg. May 2009;4(3):281-6. Epub Mar. 19, 2009.
Laouri et al., "The burden of disease of retinal vein occlusion: review of the literature," Eye, 2011, 25: 981-988.
Lawson et al., "Transoral robotic surgery for the management of head and neck tumors: learning curve," European archives of oto-rhino-laryngology: official journal of the European Federation of Oto-Rhino-Laryngological Societies (EUFOS): affiliated with the German Society for Oto-Rhino-Laryngology—Head and Neck Surgery 268, 12 (Dec. 2011), 1795-801.
Lazard, "On The Representation Of Rigid-Body Motions And Its Application To Generalized Platform Manipulators," Computational kinematics, 1993, pp. 175-181.
Lee et al., "Elimination-Based Solution Method for the Forward Kinematics of the General Stewart-Gough Platform," Computational Kinematics (CK2001), 2001, pp. 259-266.
Lee et al., "Human-guided surgical robot system for spinal fusion surgery: CoRASS," in 2008 IEEE International Conference on Robotics and Automation, ICRA 2008, May 19, 2008-May 23, 2008, Pasadena, CA, United States, 2008, pp. 3881-3887.
Leitner et al., "Computer-Assisted Knee Surgical Total Replacement," in Lecture Notes in Computer Science (LNCS) vol. 1205, J. Troccaz, E. Grimson, and R. Mosges, Eds.: Springer, 1997, 629-638.
Li et al., "Design and Study of a Novel Hyper-Redundant Manipulator," Robotica, 2003, vol. 21, pp. 505-509.
Li et al., "Spatial Motion Constraints in Medical Robot Using Virtual Fixtures Generated by Anatomy," in IEEE International Conference on Robotics & Automation, 2004, pp. 1270-1275.
Li et al., "A miniature B-scan forward-imaging OCT probe to guide real-time laser ablation," in Association for Research in Vision and Ophthalmology (ARVO) Annual Meeting, 2012.
Li et al., "Design of Continuous Backbone, Cable-Driven Robots," 2002, vol. 124, pp. 265-271.
Li et al., "Feasibility study on bonding quality inspection of microfluidic devices by optical coherence tomography," J. Biomed. Opt., 2011, 16(6): 066011, 9 pages.
Li et al., "Miniature forward-imaging B-scan optical coherence tomography probe to guide real-time laser ablation," Lasers Surg. Med., 2014, vol. 46, No. 3, pp. 193-202.

(56) References Cited

OTHER PUBLICATIONS

Lim et al., "Future of active catheters," Sensors and Actuators, 1996, vol. 56, pp. 113-121.
Lim et al., "Multi-link active catheter snake-like motion," Robotica, 1996, vol. 14, pp. 499-506.
Lipkin et al., "Hybrid Twist and Wrench Control for a Robotic Manipulator," Transaction of the ASME 110 (1988), 138-144.
Lipska et al., "Anastomotic leakage after lower gastrointestinal anastomosis: men are at a higher risk," Anz J. Surg., 2006, vol. 76, No. 7, pp. 579-585.
Liu et al., "Learning Insertion Task of a Flexible Beam by Virtual Agents," IEEE International Conference on Robotics and Automation, 2002, pp. 3290-3295.
Lock et al., "Friction Modeling in Concentric Tube Robots," In 2011 IEEE International Conference on Robotics and Automation (Shanghai, China, Jan. 2011), pp. 1139-1146.
Lohmeyer et al., "Prospective clinical study on digital nerve repair with collagen nerve conduits and review of literature," J. Reconstr. Microsurg., 2014, vol. 30, pp. 227-234.
Lumelsky et al., "Real-Time Collision Avoidance in Tele-operated Whole-Sensitive Robot Arm Manipulators," IEEE Transactions on Systems, Man, and Cybernetics 23, 1 (1993), 194-203.
Ma et al., "An obstacle avoidance scheme for hyper-redundant manipulators-global motion planning in posture space," In Proceedings of International Conference on Robotics and Automation (1997), vol. 1, IEEE, pp. 161-166.
Ma et al., "Architecture Singularities of Parallel Manipulators," IEEE International Conference on Robotics and Automation, 1991, pp. 1542-1547.
Maden et al., "A review of planar scissor structural mechanisms: geometric principles and design methods," Architectural Science Review, 2011, vol. 54, No. 3, pp. 246-257.
Mader et al., "Ocular war injuries of the Iraqi insurgency," Jan. Sep. 2004. Ophthalmology, 2006, 113:97-104.
Maeda et al., "Active endoscope with SMA (Shape Memory Alloy) coil springs," in Proc. IEEE 9th Int. Workshop Microelectromech. Syst., San Diego, CA, 1996, pp. 290-295.
Mahvash et al., "Friction Compensation for a Force-Feedback Telerobotic System," In 2006 IEEE International Conference on Robotics and Automation (Orlando, FL, 2006), No. May, pp. 3268-3273.
Mahvash et al., "Mechanics of dynamic needle insertion into a biological material," IEEE transactions on bio-medical engineering 57, 4 (Apr. 2010), 934-43.
Mahvash et al., "Stiffness Control of a Continuum Manipulator in Contact with a Soft Environment," The 2010 IEEE/RSJ International Conference on Intelligent Robots and Systems (Oct. 18-22, 2010).
Mahvash et al., "Stiffness Control of Surgical Continuum Manipulators," IEEE Transaction on Robotics 27, 2 (2011), 334-345.
Manolidis et al., "Do the genes that cause otosclerosis reduce susceptibility to otitis media?" Otol Neurotol, 2003, vol. 24, pp. 868-871.
Manolidis et al., "Use of reconstructed, nonorthogonal plane, high-resolution computed tomography of the temporal bone in the planning of temporal bone surgery," ORL J Otorhinolaryngol Relat Spec, 2003, vol. 65, pp. 71-75.
Manolidis et al., "Robotic insertion of cochlear implant electrodes to minimize cochlear trauma." 6th European Congress of Oto—Rhino—Laryngology, Head & Neck Surgery, Vienna, Austria, 2007.
Mason et al., "Sheathotomy to decompress branch retinal vein occlusion: a matched control study," Ophthalmology, 2004, vol. 111, pp. 540-545.
Mason et al., "Robot Hands and the Mechanics of Manipulation," MIT Press, Cambridge, MA, 1985.
Mason, "Compliance and Force Control for Computer Controlled Manipulators," IEEE Transaction on Systems, Vlan, and Cybernetics smc-11, 6 (1981), 418-432.
Matsumoto et al., "Collision Detection of Manipulator Based on Adaptive Control Law," In 2001 IEEE/ASME International Conference on Advanced Intelligent Mechatronics (Como, Italy, 2001), pp. 177-182.
Matsumura et al., "Microvascular anastomosis at 30-50x magnifications (super-microvascular anastomosis) in neurosurgery," Surg. Neurol. Int., 2011, vol. 2, 6 pages.
Matsunaga et al., "Histopathologic evaluation of the internal limiting membrane surgically excised from eyes with diabetic maculopathy," Retina, 2005, vol. 25, pp. 311-316.
McIntosh et al., "Interventions for branch retinal vein occlusion: an evidence-based systematic review," Ophthalmology, 2007, vol. 114, pp. 835-854.
McMahan et al., "Field trials and testing of the octarm continuum manipulator," in Robotics and Automation, 2006. ICRA 2006. Proceedings 2006 IEEE International Conference on. IEEE, 2006, pp. 2336-2341.
Meeker et al., "Optimal Realization of Arbitrary Forces in a Magnetic Sterotaxis System," IEEE Transactions on Magnetics, 1996, vol. 32, pp. 320-328.
Merlet, "An Initiative for The Kinematic Study of Parallel Manipulators," Proceedings of the Workshop on Fundamental Issues and Future Research Directions for Parallel Mechanisms and Manipulators, 2002, 8 pages.
Merlet, "Kinematics is Not Dead!" IEEE International Conference on Robotics and Automation, 2000, pp. 1-6.
Merlet, "Parallel manipulators: state of the art and perspective," Journal of Robotics Society of Japan, 1992, vol. 10, pp. 57-62.
Merlet, "Parallel Robots: Open Problems," 9th International Symposium of Robotics Research, Snowbird, 1999, pp. 23-28.
Merlet, "Singular configurations of parallel manipulators and Grassmann geometry," in Geometry and Robotics, vol. LNCS 391, B. J-D. and J-P.Laumond, Eds., 1989, pp. 194-212.
Merlet, "Singular configurations of parallel manipulators and Grassmann geometry," Int. J. of Robotics Research, 1989, vol. 8, pp. 45-56.
Merzouki et al., "Compensation of friction and backlash effects in an electrical actuator," J. Syst. Cont. Eng., 2004, vol. 218, No. 2, 10 pages.
Mester et al., "Vitrectomy with aiteriovenous decompression and internal limiting membrane dissection in branch retinal vein occlusion," Retina, 2002, vol. 22, pp. 740-746.
Mikhail et al., "Robotic-assisted laparoscopic prostatectomy: first 100 patients with one year of follow-up.," Urology, 2006, vol. 68, No. 6, pp. 1275-1279.
Mineta, "Batch fabricated flat meandering shape memory alloy actuator for active catheter," Sensors and Actuators A, 2001, vol. 88, pp. 112-120.
Mochiyama et al., "Direct Kinematics of Manipulators with Hyper Degrees of Freedom and Fernet-Serret Formula," International Conference on Robotics and Automation, 1998, pp. 1653-1658.
Mochiyama et al., "Shape Correspondence between a Spatial Curve and a Manipulator with Hyper Degrees of Freedom," IEEE/RSJ International conference on Intelligent Robots and Systems (IROS'), 1998, pp. 161-166.
Mochiyama et al., "The Shape Jacobian of a Manipulator with Hyper Degrees of Freedom," IEEE International Conference on Robotics and Automation, 1999, pp. 2837-2842.
Mochiyama et al., "Shape Control of Manipulators with Hyper Degrees of Freedom," Int. J. Robot. Res., 1999, vol. 18, No. 6, pp. 584-600.
Moll et al., "Path Planning for Variable Resolution Minimal-Energy Curves of Constant Length," IEEE International Conference on Robotics and Automation, Barcelona, Spain, 2005, pp. 2130-2135.
Möller, "Gröbner Bases and Numerical Analysis," in Gröbner Bases and Applications, Lecture Note Series 251—London Mathematical Society, B. Buchberger and F. Winkler, Eds., 1998, pp. 159-178.
Montesi et al., "An SMA-base flexible active endoscope for minimal invasive surgery," Journal of Micromechanics and Microengineering, 1995, vol. 5, pp. 180-182.
Nagatsu et al., "Macro-micro bilateral control using Kalman filter based state observer for noise reduction and decoupling of modal space," in IECON 2013—39th Annual Conference of the IEEE Industrial Electronics Society, 2013, pp. 4192-4197.

(56) References Cited

OTHER PUBLICATIONS

Nakagaki et al., "Study of insertion Task of a Flexible Beam into a Hole," IEEE International Conference on Robotics and Automation, 1995, pp. 330-335.

Nakagaki et al., "Study of Insertion Task of a Flexible Wire into a Hole by Using Visual Tracking Observed by Stereo Vision," IEEE International Conference on Robotics and Automation, 1996, pp. 3209-3214.

Nakamura et al., "A robotic neurosurgery system with autofocusing motion control for mid-infrared laser ablation," in MICCAI'2006 workshop on medical robotics, Copenhagen, Denmark, 2006, pp. 108-115.

Nakamura et al., "Inverse Kinematic Solutions With Singularity Robustness for Robot Manipulator Control," J. Dyn. Syst. Meas. Control, 1986, vol. 108, No. 3, p. 163-171.

Nakamura, "Advanced Robotics: Redundancy and Optimization," Addison-Wesley Longman Publishing Co., Inc., Boston, MA, USA, 1990.

Nguyen et al., "A tendon-driven continuum robot with extensible sections," in Intelligent Robots and Systems (IROS), 2015 IEEE/RSJ International Conference on. IEEE, 2015, pp. 2130-2135.

NIDCD, "Presbycusis according to NIDCD," 2016, <https://www.nidcd.nih.gov/sites/default/files/Content%20Images/presbycusis.pdf>.

Nielsen et al., "Solving the Input/Output Problem for Planar Mechanisms," ASME J. of Mechanical Design, 1999, vol. 121, pp. 206-211.

Nukherjee, "Design of holonomic loops for repeatability in redundant manipulators," in Proceedings of 1995 IEEE International Conference on Robotics and Automation, vol. 3, pp. 2785-2790.

Oghalai et al., "Neonatal hearing loss in the indigent," Laryngoscope, 2002, vol. 112, pp. 281-286.

Oh et al., "Long-term visual outcome of arteriovenous adventitial sheathotomy on branch retinal vein occlusion induced macular edema," Korean J Ophthalmol, 2008, vol. 22, pp. 1-5.

Okie, "Traumatic brain injury in the war zone," N Engl J Med, 2005, 352(20):2043-2047.

Olsson et al., "Friction Models and Friction Compensation," European Journal of Control, 1998, vol. 4, No. 3, pp. 176-195.

O'Malley et al., "Robotic Anterior and Midline Skull Base Surgery: Preclinical Investigations," Int. J. Radiation Oncology Biol. Phys., 2007, vol. 69, pp. 2125-2128.

Opremcak, "Surgical decompression of branch retinal vein occlusion via arteriovenous crossing sheathotomy: a prospective review of 15 cases," Retina, 1999, vol. 19, pp. 1-5.

Osterloh, "Surgical decompression of branch retinal vein occlusions," Arch Ophthalmol., 1988, vol. 106, pp. 1469-1471.

Osuka et al., "Development of Mobile Inspection Robot for Rescue Activities: MIORA," IEEE/RSJ International Conference on Intelligent Robots and Systems, 2003, pp. 3373-3377.

Ota et al., "A Novel Highly Articulated Robotic Surgical System For Epicardial Ablation," in 30th Annual International IEEE EMBS Conference, Vancouver, British Colombia, Canada, 2008, pp. 250-253.

Paljug et al., "The JPL Serpentine Robot: a 12 DOF System for Inspection," IEEE Int. Conf. on Robotics and Automation, 1995, pp. 3143-3148.

Pantuck et al., "A Novel Resectoscope for Transurethral Resection of Bladder Tumprs and the Prostate," The Journal of Urology, 2007, vol. 178, 2331-2336.

Park et al., "A multilink active catheter with polyimide-based integrated CMOS interface circuits," Journal of Micromechanical Systems, 1999, pp. 349-357.

Park et al., "Macular hole surgery with internal-limiting membrane peeling and intravitreous air," Ophthalmology, 1999, vol. 106(7), pp. 1392-1397.

Park et al., "Robot Multiple Contact Control," Robotica 26, 05 (2008), 667-677.

Patrick et al., "Characterization of mechanical properties of single electrodes and multi-electrodes," Annals of Otology, Rhinology and Laryngologyment, 1987, vol. 96, pp. 46-48.

Patronik et al., "Crawling on the heart: a mobile robotics device for minimally invasive cardiac interventions," in MICCAI 2004 (7th International Conference on Medical Image Computing and Computer-Assisted Intervention), 2004, pp. 9-16.

Peersman et al., "Prolonged operative time correlates with increased infection rate after total knee arthroplasty," HSS J., 2006, vol. 2, No. 1, pp. 70-72.

Peirs et al., "Design of an Advanced Tool Guiding System for Robotic Surgery," in 2003 IEEE International Conference on Robotics and Automation, 2003, pp. 2651-2656.

Penning et al., "Towards Closed Loop Control of a Continuum Robotic Manipulator for Medical Applications," In 2011 IEEE International Conference on Robotics and Automation (Shanghai, China 2011), pp. 4822-4827.

Petrovskays et al., "Probabilistic Estimation of Whole Body Contacts for Multi-Contact Robot Control," In 2007 IEEE International Conference on Robotics and Automation (Rome, 2007), No. c, pp. 568-573.

Phee et al., "Analysis and Development of Locomotion Devices for the Gastrointestinal Tract," IEEE Transactions on Biomedical Engineering, 2002, vol. 49, pp. 613-616.

Phee et al., "Robotic system for no-scar gastrointestinal surgery," The international journal of medical robotics + computer assisted surgery: MRCAS 4, 1 (Mar. 2008), 15-22.

Phelan et al., "Laparoscopic partial nephrectomy and minimally invasive nephron-sparing surgery," Current urology reports, 2003, vol. 4, pp. 13-20.

Phillips et al., "Closed globe macular injuries after blasts in combat," Retina, 2013, 33(2):371-9.

Piccigallo et al., "Design of a Novel Bimanual Robotic System for Single-Port Laparoscopy," IEEE/ASME Transaction on Mechatronics 15, 6 (2010), 871-878.

Pickens et al., "Preliminary Testing of a Transurethral Dexterous Robotic System for Bladder Resection," In 27th EUS Annual Meeting, pp. 65. Atlanta, GA 2012.

Pickens et al., "A Pilot Ex-Vivo Evaluation of a Telerobotic System for Transurethral Intervention and Surveillance," J. Endourol., 2015, 29(2): 231-234.

Pile et al., "Algorithms and Design Considerations for Robot Assisted Insertion of Perimodiolar Electrode Arrays," In 2011 IEEE International Conference on Robotics and Automation. Shanghai, China 2011.

Pile et al., "Characterization of Friction and Speed Effects and Methods for Detection of Cochlear Implant Electrode Tip Foldover," In Accepted for publication in IEEE International Conference on Robotics and Automation (ICRA'2013).

Pile et al., "Speed Dependence of Insertion Forces During CI Electrode Insertion," In Presented at the 12th Annual Conference on Cochlear Implants and other Implantable Auditory Technologies CI'2012, Baltimore, MD, May 3-5, 2012.

Piltan et al., "Design Gradient Descent Optimal Sliding Mode Control of Continuum Robots," IAES Int. J. Robot. Autom., 2012, vol. 1, No. 4, pp. 175-189.

Popov et al., "Towards variable stiffness control of antagonistic twisted string actuators," In Intelligent Robots and Systems (IROS 2014), 2014 IEEE/RSJ International Conference, 2014, pp. 2789-2794.

Porpiglia, "Editorial comments to da Vinci-assisted robotic partial nephrectomy: technique and results at a mean of 15 months of follow-up," European urology, 2007, vol. 51, p. 191.

Portman et al., "Rigid 6-DOF parallel platform for precision 3-D micromanipulation," Int. J. Mach. Tools Manuf., 2001, vol. 41, No. 9, pp. 1229-1250.

Prasad et al., "Surgical robotics: impact of motion scaling on task performance," J. Am. Coll. Surg., 2004, vol. 199, No. 6, pp. 863-868.

Pritts et al., "Design of an artificial muscle continuum robot," in Robotics and Automation, 2004. Proceedings. ICRA'04. 2004 IEEE International Conference on, vol. 5. IEEE, 2004, pp. 4742-4746.

(56) References Cited

OTHER PUBLICATIONS

Quiram et al., "Outcomes of vitrectomy with inferior retinectomy in patients with recurrent rheg matogenous retinal detachments and proliferative vitreoretinopathy," Ophthalmology, 2006, 113:2041-2047.
Raghavan et al., "Solving Polynomial Systems for the Kinematic Analysis and Synthesis of Mechanisms and Robot Manipulators," ASME J. of Mechanical Design, 1995, vol. 117, pp. 71-79.
Raghavan, "The Stewart Platform of General Geometry Has 40 Configurations," ASME J. of Mechanical Design, 1993, vol. 115, pp. 277-282.
Raibert et al., "Hybrid Position/Force Control of Manipulators," Journal of Dynamic Systems, Measurement, and Control 103, 2 (1981), 126.
Rehak, "Branch retinal vein occlusion: pathogenesis, visual prognosis, and treatment modalities," Curr Eye Res, 2008, vol. 33, pp. 111-131.
Reichert et al., "Robotic insertion of cochlear implant electrodes to minimize cochlear trauma," In 6th European Congress of Oto-Rhino-Laryngology, Head and Neck Surgery., Vienna, Austria, Jun. 2007.
Reiter et al., "A Learning Algorithm for Visual Pose Estimation of Continuum Robots," In 2011 IEEE/RSJ International Conference on Intelligent Robots and Systems (San Francisco, CA, USA, 2011), pp. 2390-2396.
Reiter et al., "Learning-Based Configuration Estimation of a Multi-Segment Continuum Robot," In the Fourth IEEE RAS/EMBS International Conference on Biomedical Robotics and Biomechatronics (Roma, Italy, 2012), p. accepted.
Reynaerts et al., "Shape memory micro-actuation for a gastrointestinal intervention system," Sensors and Actuators, vol. 77, pp. 157-166, 1999.
Rhode, "Large Deflections of Cantilever Beam with Uniformly Distributed Load," Q. Appl. Math., 1953, vol. 11, pp. 337-338.
Rivera-Serrano et al., "A transoral highly flexible robot: Novel technology and application," The Laryngoscope 122, 5 (May 2012), 1067-71.
Roberts et al., "A comparison of two methods for choosing repeatable control strategies for kinematically redundant manipulators," in Proceedings 1992 IEEE International Conference on Robotics and Automation, 1992, pp. 514-519.
Robinson et al., "Continuum robots—a state of the art," In 1999 IEEE International Conference on Robotics and Automation (Detroit, MI, USA, 1999), vol. 4, IEEE, pp. 2849-2854.
Rodanant et al., "Sheathotomy without separation of venule overlying arteriole at occlusion site in uncommon branch retinal vein occlusion," J Med Assoc Thai., 2005, vol. 88, pp. 143-150.
Rogers et al., "Robotic partial nephrectomy for renal hilar tumors: a multi-institutional analysis," The Journal of urology, 2008, vol. 180, discussion 2356, pp. 2353-2356.
Rogers et al., "Robotic partial nephrectomy: the real benefit," Current opinion in urology, 2011, vol. 21, pp. 60-64.
Rogers et al., "The prevalence of retinal vein occlusion: pooled data from population studies from the United States, Europe, Asia, and Australia," Ophthalmology, 2010, vol. 117, pp. 313-319.
Roland et al., "Progress Towards a Robotically Inserted Cochlear Implant Electrode," In 12th Symposium on Cochlear Implants in Children, Seattle 2009.
Roland, "A model for cochlear implant electrode insertion and force evaluation: results with a new electrode design and insertion technique," The Laryngoscope, 2005, vol. 115, pp. 1325-1339.
Rone et al., "Continuum Manipulator Statics Based on the Principle of Virtual Work," in vol. 4: Dynamics, Control and Uncertainty, Parts A and B, 2012, 8 pages.
Rosenberg, "Virtual fixtures: Perceptual tools for telerobotic manipulation," in Proceedings of IEEE Virtual Reality Annual International Symposium, 1993, pp. 76-82.
Roth, "Computation in Kinematics," Computational Kinematics, 1993, pp. 3-14.
Roy et al., "Investigation of effects of dynamics on intrinsic wrench sensing in continuum robots," in Robotics and Automation (ICRA), 2016 IEEE International Conference on. IEEE, 2016, pp. 2052-2059.
Rucker et al., "Deflection-Based Force Sensing for Continuum Robots: A Probabilistic Approach," In 2011 IEEE/RSJ International Conference on Intelligent Robots and Systems (2011), pp. 3764-3769.
Rucker et al., "Geometrically Exact Model for Externally Loaded Concentric-Tube Continuum Robots," IEEE Transaction on Robotics 26, 5 (2010), 769-780.
Rucker et al., "Statics and Dynamics of Continuum Robots With General Tendon Routing and External Loading," IEEE Trans. Robot., 2011, vol. 27, No. 6, pp. 1033-1044.
Rul et al., "A Novel Tool Using SMA Actuator for cell puncturing," in SICE Annual Conference 2007, 2007, pp. 254-258.
Russo et al., "A Novel Robotic Platform for Laser Assisted Transurethral Surgery of the Prostate," IEEE Trans. Biomed. Eng., vol. 9294, No. c, pp. 1-12, 2014.
Safarik, "Editorial comments to da Vinci-assisted robotic partial nephrectomy: technique and results at a mean of 15 months of follow-up," European urology, 2007, vol. 51, p. 192.
Saito, "Transurethral en bloc resection of bladder tumors," The Journal of Urology 166,6 (Dec. 2001), 2148-50.
Salerno et al., "Design Considerations for a Minimally Invasive High-Throughput Automation System for Radiation Biodosimetry," In IEEE Conference on Automation Science and Engineering, pp. 846-852. Scottsdale, AZ, USA 2007.
Salisbury et al., "Preliminary design of a whole-arm manipulation system (WAMS)," in Proc. IEEE Int. Conf. Robot. Autom., Philadelphia, PA, 1988, pp. 254-260.
Salisbury, Active stiffness control of a manipulator in cartesian coordinates. In 1980 19th IEEE Conference on Decision and Control including the Symposium on Adaptive Processes (1980), pp. 95-100.
Sanchez et al., "New master arm for transurethral resection with a robot," Arch. Españoles Urol., 2002, vol. 55, No. 10, pp. 1247-1250.
Saraf, "Robotic Assisted Microsurgery (RAMS): Application in Plastic Surgery," in Medical Robotics, V. Bozovic, Ed. 2008, pp. 364-376.
Schnider et al., "PADyC: a Synergetic Robot for Cardiac Puncturing," in IEEE International Conference on Robotics and Automation, San Francisco, CA, 2000, pp. 2883-2888.
Scholkopf et al., "New support vector algorithms," Neural Comput., 2000, vol. 12, No. 5, pp. 1207-1245.
Schriber, "Volvo Chooses Spine Robot for Spray Operations," in Robotics Today, 1984, pp. 28.
Schurzig et al., "A force sensing Automated Insertion Tool for cochlear electrode implantation," in IEEE International Conference on Robotics and Automation, 2010, pp. 3674-3679.
Scott et al., "A randomized trial comparing the efficacy and safety of intravitreal triamcinolone with standard care to treat vision loss associated with macular Edema secondary to branch retinal vein occlusion: the Standard Care vs Corticosteroid for Retinal Vein Occlusion (SCORE) study report 6," Arch Ophthalmol, 2009, vol. 127, pp. 1115-1128.
Sears et al., "Inverse Kinematics of Concentric Tube Steerable Needles," 2007, pp. 1887-1892.
Seibold et al., "Prototype of Instrument for Minimally Invasive Surgery with 6-Axis Force Sensing Capability," In Proceedings of the 2005 IEEE International Conference on Robotics and Automation (Barcelona, Spain, 2005), 496-501, Ed., IEEE, pp. 496-501.
Sen et al., "Enabling technologies for natural orifice transluminal endoscopic surgery (N.O.T.E.S) using robotically guided elasticity imaging," In Proceeding of SPIE Medical Imaging 2012, pp. 83161Y1-83161Y8.
Sentis et al., "Compliant Control of Multicontact and Center-of-Mass Behaviors in Humanoid Robots," IEEE Transactions on Robotics 26, 3 (Jun. 2010), 483-501.
Shah et al., "Adventitial sheathotomy for treatment of macular edema associated with branch retinal vein occlusion," Curr Opin Ophthalmol, 2000, vol. 11, pp. 171-174.

(56) References Cited

OTHER PUBLICATIONS

Shahinpoor et al., "Ionic Polymer-Metal Composites (IPMC) as biomimetic sensors and actuators," Proc. SPIE's 5th Int'l Symp. On Smart Structures and Materials, 1998, pp. 251-267.

Shamir et al., "Repeatability of redundant manipulators: mathematical solution of the problem," IEEE Trans. Automat. Contr., 1988, vol. 33, No. 11, pp. 1004-1009.

Shamir, "An overview on the global behavior of kinematically redundant robotic manipulators," in Eighteenth Convention of Electrical and Electronics Engineers in Israel, 1995, pp. 2.3.1/1-2.3.1/6.

Shamir, "Remarks on some dynamical problems of controlling redundant manipulators," IEEE Trans. Automat. Contr., 1990, vol. 35, No. 3, pp. 341-344.

Shen et al., "A Robotic-controlled Intraocular OCT Probe," In 2013 The Association for Research in Vision and Ophthalmology Annual Conference (ARVO'2013).

Shen et al., "An intraocular OCT probe," in Association for Research in Vision and Ophthalmology (ARVO) Annual Meeting, 2011.

Shen et al., "Comparison of imaging a retinal mimicking phantom through air and vitreous substitutes with a 25-gauge B-scan OCT endoprobe versus an 18 mm telecentric OCT probe," in Association for Research in Vision and Ophthalmology (ARVO) Annual Meeting, 2014.

Shiakolas et al., "On the Accuracy, Repeatability, and Degree of Influence of Kinematics Parameters for Industrial Robots," Int. J. Model. Simul., 2002, vol. 22, No. 3, 10 pages.

Shoham et al., "Bone-Mounted Miniature Robot for Surgical Procedures: Concept and Clinical Applications," IEEE Transactions on Robotics and Automation, 2003, vol. 19, pp. 893-901.

Shoham et al., "Robot Construction for Surgery," First Israeli Symposium on Computer-Aided Surgery, Medical Robotics, and Medical Imaging (ISRACAS'98), Technion City, Haifa, Israel, 1998.

Siciliano et al., "Robotics: Modelling, Planning, and Control," 2009.

Simaan et al., "A Dexterous System for Laryngeal Surgery—Multi-Backbone Bending Snake-like Slaves for Teleoperated Dexterous Surgical Tool Manipulation." pp. 351-357, 2004.

Simaan et al., "A Dual-Arm Workstation for Intraocular Dexterity-Enhanced Microsurgery of the Eye and In-Organ Dexterity Enhancement and Manipulation of Suspended Organs," 2006.

Simaan et al., "Design and Integration of a Telerobotic System for Minimally Invasive Surgery of the Throat," International Journal of Robotics Research (IJRR) special issue on medical robotics. doi: 10.1177/0278364908104278, vol. 28, No. 9, 1134-1153, 2009.

Simaan et al., "Design Considerations of New Six Degrees-Of-Freedom Parallel Robots," In IEEE International Conference on Robotics and Automation (ICRA'1998), pp. 1327-1333.

Simaan et al., "Geometric Interpretation of the Derivatives of Parallel Robot's Jacobian Matrix with Application to Stiffness Control" ASME Journal of Mechanical Design, vol. 125, pp. 33-42., doi: 10.1115/1.1539514, 2003.

Simaan et al., "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.

Simaan et al., "Inroads towards a robotically inserted CI electrode development," In 9th European Symposium of Paediatric Cochlear Implantation, 2009.

Simaan et al., "Lessons learned using the insertable robotic effector platform (IREP) for single port access surgery," Journal of Robotic Surgery, Apr. 2013.

Simaan et al., "Minimally Invasive Surgery of the Upper Airways: Addressing the Challenges of Dexterity Enhancement in Confined Spaces," Nova Scien, R. Faust, Ed. 2007, pp. 261-280.

Simaan et al., "Remarks on Hidden Lines in Parallel Robots," 7th International Symposium on Advances in Robot Kinematics (ARK 2000), Piran-Portoroz, Slovenia, 2000.

Simaan et al., "Robot Construction for Surgical Applications," The 1st IFAC Conference on Mechatronic Systems, Darmstadt, Germany, 2000, pp. 553-558.

Simaan et al., "Robotic Study Shows that Insertion Speed Affects cochlear Implant Electrode Insertion Forces," In the 11th International Conference on Cochlear Implants and other Implantable Auditory Technologies, Stockholm, Sweden, Jun. 30-Jul. 3, 2010.

Simaan et al., "Robotic System for Steerable Cochlear Implant Insertion," In 2011 National Congress of the Italian Society of Audiology & Phoniatrics in Bari, Italy 2011.

Simaan et al., "Singularity Analysis of a Class of Composite Serial In-Parallel Robots," IEEE transactions on Robotics and Automation, vol. 17, No. 3, pp. 301-311, doi:10.1109/70.938387 Jun. 2001.

Simaan et al., "Steerable Continuum Robot Design for Cochlear Implant Surgery," In IEEE International Conference on Robotics and Automation Workshop on Snakes, Worms and Catheters: Continuum and Serpentine Robots for Minimally Invasive Surgery, May 3. 2010.

Simaan et al., "Stiffness Synthesis of a Variable Geometry Planar Robot," Advances in Robot Kinematics: Theory and Applications, 2002, pp. 463-472.

Simaan et al., "Stiffness Synthesis of a Variable Geometry Six Degrees-of-Freedom Double Planar Parallel Robot," International Journal of Robotics Research (IJRR), vol. 22, No. 9, pp. 757-775, doi: 10.1177/02783649030229005, Sep. 2003.

Simaan, "Analysis and Synthesis of Parallel Robots for Medical Applications," Master Thesis. Technion—Israel Institute of Technology, Haifa, Israel, 1999.

Simaan, "Design Considerations and Lessons Learned in Developing Systems for Single Port Access Surgery and Natural Orifice Surgery," In 34th international Conference on Engineering in Medicine and Biology Society (mini-symposium on Robotic Single-Port Surgery and Notes). San Diego, Aug. 27-31, 2012.

Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.

Simaan, "Task-Based Design and Synthesis of Variable Geometry Parallel Robots," (2002). Phd Thesis, Technion-Israel Institute of Technology, Haifa, Israel.

Slutsky, "The management of digital nerve injuries," J. Hand Surg. Am., 2014, vol. 39, pp. 1208-1215.

Smiddy et al., "Internal limiting membrane peeling in macular hole surgery," Ophthalmology, 2001, vol. 108(8), pp. 1471-1476.

Smiddy, "Economic Considerations of Macular Edema Therapies," Ophthalmology, 2011, pp. 1827-1833.

Soper et al., "Surface mosaics of the bladder reconstructed from endoscopic video for automated surveillance," IEEE Trans. Biomed. Eng., 2012, vol. 59, No. 6, pp. 1670-1680.

Stetter, "Multivariate Polynomial Equations as Matrix Eigenproblems," Contributions in Numerical Mathematics, World Scientific Series in Applicable Analysis (WSSIAA), 1993, pp. 355-371.

Stewart, "A Platform With Six Degrees-of-Freedom," The Institution of Mechanical Engineers, Proceedings 1965-66, 1965, 180(15): 371-386.

Sturges et al., "A flexible, tendon-controlled device for endoscopy," 1991, vol. 3, pp. 2582-2591.

Su et al., "A MRI-Guided Concentric Tube Continuum Robot with Piezoelectric Actuation: A Feasibility Study," In 2012 IEEE International Conference on Robotics and Automation, pp. 1939-1945.

Su et al., "Augmented Reality During Robot-assisted Laparoscopic Partial Nephrectomy: Toward Real-Time 3D-CT to Stereoscopic Video Registration," Urology, 2009, vol. 73, pp. 896-900.

Sung et al., "Robotic Laparoscopic Surgery: a Comparison of the DA Vinci and Zeus Systems," Urology, 2001, vol. 58, pp. 893-898.

Suthakorn et al., "A New Inverse Kinematics Algorithm for Binary Manipulators with Many Actuators," Advanced Robotics, 2001, vol. 15, pp. 225-244.

Suzumori et al., "A Miniature Inspection Robot Negotiating Pipes of Widely Varying Diameter," IEEE International Conference on Robotics and Automation, 2003, pp. 2735-2740.

(56) References Cited

OTHER PUBLICATIONS

Suzumori et al., "Applying a Flexible Microactuator to Robotic Mechanisms," EEE robotics and Automation Magazine, 1992, vol. I, pp. 21-27.
Suzumori et al., "Development of Flexible Microactuators and Its Applications to Robotic Mechanisms," IEEE International Conference on Robotics and Automation, 1991, pp. 1622-1627.
Suzumori et al., "Flexible Microactuator for Miniature Robots," IEEE International Conference on Robotics and Automation, 1991, pp. 204-209.
Takahashi et al., "The development of an in-pipe microrobot applying the motion of an earthworm," 5th International Symposium on Micro Machine and Human Science, 1994, pp. 35-40.
Tatlicioglu et al., "Dynamic Modelling for Planar Extensible Continuum Robot Manipulators," in Proc. IEEE Int. Conf. Robot. Autom., 2007, pp. 1357-1362.
Taylor et al., "An image-directed robotic system for precise Orthopedic surgery," IEEE Transactions on Robotics and Automation, 1994, vol. 10, pp. 261-275.
Taylor et al., "Steady-hand robotic system for microsurgical augmentation," International Journal of Robotics Research, vol. 18, No. 12, pp. 1201-1210, 1999.
Thorne et al., "Chechlear Fluid Space Dimensions for Six Species Derived From Reconstructions of Three-Dimensional Magnetic Resonance Images," The Laryngeoscope, 1999, vol. 109, pp. 1661-1668.
Tonini et al., "Auditory steady-state response audiometry in profound SNHL: the impact of abnormal middle ear function," Ear Nose Throat J, 2005, vol. 84, pp. 282, 284-6, 288.
Torres et al., Motion Planning for Concentric Tube Robots Using Mechanics-based Models. In 2011 IEEE/RSJ International Conference on Intelligent Robots and Systems (San Francisco, CA, USA, 2011), pp. 5153-5159.
Trejos et al., "Port placement for endoscopic cardiac surgery based on robot dexterity optimization," Barcelona, Spain, 2005, pp. 912-917.
Trivedi et al., "Model-Based Shape Estimation for Soft Robotic Manipulators: The Planar Case," J. Mech. Robot., 2014, vol. 6, No. 2, pp. 021005-1-021005-11.
Tsai et al., "Solving the Kinematics of the Most General Six-and Five-Degrees-ofFreedom Manipulators by Continuation Methods," ASME Transactions on of Mechanisms, Transmissions, and Automation in Design, 1985, vol. 107, pp. 189-200.
Tsukagoshi et al., "Active hose: an artificial elephant's nose with maneuverability for rescue operation," in Proc. IEEE Int. Conf. Robot. Autom., Seoul, Korea, 2001, pp. 2454-2459.
Tully et al., "Constrained Filtering with Contact Detection Data for the Localization and Registration of Continuum Robots in Flexible Environments," In 2012 IEEE International Conference on Robotics and Automation (St. Paul, MI USA, 2012).
U.S. Office action for U.S. Appl. No. 13/891,389 dated Jan. 2, 2015.
U.S. Office action for U.S. Appl. No. 14/271,418 dated May 20, 2015.
Ueta et al., "Robot-assisted vitreoretinal surgery: development of a prototype and feasibility studies in an animal model," Ophthalmology, 2009, vol. 116, pp. 1538-1543.
Ukai et al., "A new technique for transurethral resection of superficial bladder tumor in 1 piece.," The Journal of Urology 2 163, 3 (2000), 878-879.
Valdastri et al., "Integration of a miniaturised triaxial force sensor in a minimally invasive surgical tool," IEEE transactions on biomedical engineering 53, 11 (Nov. 2006), 2397-400.
Van Den Heuvel et al., "Robotic assistance in microvascular surgery," in Medical Robotics, V. Bozovic, Ed. 2008, pp. 471-480.
Wagner et al., The Benefits of Force Feedback in Surgery: Examination of Blunt Dissection. Presence: Teleoperators and Virtual Environments 16, 3 (2007), 252-262.
Wakahara et al., "A Computer Aided Manipulation System for a Multijoint Inspection Robot," Proceedings of the 32nd Conference on Remote System Technology, 1984, pp. 33-38.
Wakamatsu et al., "Modeling of Linear objects Considering Bend, Twist, and Extensional Deformation," IEEE International Conference on Robotics and Automation, 1995, pp. 433-438.
Wakamatsu et al., "Static Analysis of Deformable Object Grasping Based on Bounded Force Closure," IEEE International Conference on Robotics and Automation, 1996, pp. 3324-3329.
Wakamatsu et al., "Static Modeling of Deformation Based on Differential Geometry," International Journal of Robotics Research, 2004, vol. 23, pp. 293-311.
Walker et al., "A Novel "Elephant's Trunk" Robot," Proceedings of the 1999 IEEE/ASME International Conference on Advanced Intelligent Mechatronics, 1999, pp. 410-415.
Walker et al., "Some Issues in Creating 'Invertebrate' Robots," In the Proceedings of the International Symposium on Adaptive Motion of Animals and Machines, Montreal, Canada, 2000, 6 pages.
Wampler et al., "Numerical Continuation Methods for Solving Polynomial Systems Arising in Kinematics," ASME Journal of Mechanical Design, 1990, vol. 112, pp. 59-68.
Wampler et al., "Manipulator Inverse Kinematic Solutions Based on Vector Formulations and Damped Least-Squares Methods," IEEE Trans. Syst. Man. Cybern., 1986, vol. 16, No. 1, pp. 93-101.
Wampler, "Solving the Kinematics of Planar Mechanisms by Dixon Determinant and a ComplexPlane Formulation," ASME J. of Mechanical Design, 2001, vol. 123, pp. 382-387.
Wang et al., "Conceptual design and dimensional synthesis of 'MicroHand," Mechanism and Machine Theory, 2008, vol. 43, No. 9, pp. 1186-1197.
Wang et al., "Investigation of Error Propagation in Multi-Backbone Continuum Robots," in Advances in Robot Kinematics, 2014, pp. 385-394.
Wardrop et al., "A temporal bone study of insertion trauma and intracochlear position of cochlear implant electrodes I: comparison of Nucleus banded and Nucleus Contour electrodes," Hearing Research, 2005, vol. 203, pp. 54-67.
Wardrop et al., "A temporal bone study of insertion trauma and intracochlear position of cochlear implant electrodes II: comparison of spiral clariontrade mark and HiFocus Iltrade mark electrodes banded and Nucleus Contour electrodes," Hearing Research, 2005, vol. 203, pp. 68-79.
Watson et al., "In vivo time-serial multi-modality optical imaging in a mouse model of ovarian tumorigenesis," Cancer Biol. Ther., 2014, vol. 15, No. 1, pp. 42-60.
Webster,III et al., "Design and Kinematic Modeling of Constant Curvature Continuum Robots: A Review," The International Journal of Robotics Research (Jun. 2010).
Webster,III et al., "Mechanics of Precurved-Tube Continuum Robots," IEEE Transaction on Robotics 25, 1 (2009), 67-78.
Wei et al., "A compact Two-armed Slave Manipulator for Minimally Invasive Surgery of the Throat," in IEEE RAS/EMBS International Conference on Biomedical Robotics and Biomechatronics, 2006, pp. 769-774.
Wei et al., "A Pilot Study on Using a Flexible Cannula Robot for Micro-Vascular Stenting," In IEEE International Conference on Robotics and Automation Workshop on Snakes, Worms and Catheters: Continuum and Serpentine Robots for Minimally Invasive Surgery, IEEE International Conference on Robotics and 4utomation, May 3, 2010.
Wei et al., "An Intelligent Hand-Held Microsurgical Instrument for Improved Accuracy," In 23rd Annual International Conference of the IEEE Engineering in Medicine and Biology Society (Istanbul, Turkey, 2001), pp. 25-28.
Wei et al., "Design and Dexterity Evaluation for a Dual-Arm Micro-Surgical Robotic System for Orbital Manipulation and Intraocular Dexterity," IEEE Transactions on Robotics, vol. 25, No. 1, pp. 147-157, 2009.
Wei et al., "Design and Theoretical Evaluation of Micro-Surgical Manipulators for Orbital Manipulation and Intraocular Dexterity," In 2007 IEEE International Conference on Robotics and Automation, pp. 3389-3395. Roma, Italy.
Wei et al., "Design of Planar Parallel Robots With Preloaded Flexures for Guaranteed Backlash Prevention," ASME Journal of Mechanisms and Robotics (JMR), doi: 10.1115/1.4000522, vol. 2, No. 1, pp. 011012-1 to 011012-10, 2010.

(56) References Cited

OTHER PUBLICATIONS

Wei et al., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.
Wei et al., "Modeling, Force Sensing, and Control of Flexible Cannulas for Microstent Delivery," Journal of Dynamic Systems, Measurement, and Control 134, 4 (2012), 041004.
Wei et al., "Performance Evaluation for Multi-Arm Manipulation of Hollow Suspended Organs," IEEE Transactions on Robotics, vol. 25, No. 1, pp. 147-157, doi 10.1109/TRO.2008.2006865, 2009.
Wei, "Design and Implementation of High-Precision Hybrid Robotic Systems with Application for Ophthalmic Micro-Surgery," Phd Thesis, Department of Mechanical Engineering, Columbia University, New York City, NY 2010.
Weichel et al., "Chorioretinectomy for perforating or severe intraocular foreign body injuries," Graefes Arch Clin Exp Ophthalmol., 2010, 248(3):319-30.
Weichel et al., "Traumatic macular holes secondary to combat ocular trauma," Retina, 2009, 29(3):349-54.
Weinstein et al., "Transoral robotic surgery: A multicenter study to assess feasibility, safety, and surgical margins," The Laryngoscope (Jul. 2012), 1-7.
Whitney, "Force Feedback Control of Manipulator Fine Motions," Journal of Dynamic Systems, Measurement, and Control 99, 2 (1977), 91.
Whitney, "Resolved Motion Rate Control of Manipulators and Human Prostheses," IEEE Transaction on Man-Machine Systems MMS-10, 2 (Jun. 1969), 47-53.
Widran, "Video transurethral resection using controlled continuous flow resectoscope," Urology, 1988, 31(5):382-6.
Williams, "Macular holes: the latest in current management," Retina, 2006, vol. 26(6 Suppl), pp. S9-12.
Wolf et al., "A Mobile Hyper Redundant Mechanism for Search and Rescue Tasks," IEEE/RSJ International Conference on Intelligent Robots and Systems, 2003, pp. 2889-2895.
Wolf et al., "MBARS: Mini bone attached robotic system for joint arthroplasty," Pisa, Italy, 2006, pp. 1053-1058.
Xu et al., "A Pilot Investigation of Continuum Robots as a Design Alternative for Upper Extremity Exoskeletons," In IEEE International Conference on Robotics and Biomimetics (ROBIO'2011), pp. 656-662.
Xu et al., "Actuation Compensation for Flexible Surgical Snake-like Robots with Redundant Remote Actuation," in IEEE International Conference on Robotics and Automation, 2006, pp. 4148-4154.
Xu et al., "An Investigation of the Intrinsic Force Sensing Capabilities of Continuum Robots," IEEE Transactions on Robotics (TRO), vol. 23, No. 3 (Jun. 2008).
Xu et al., "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.
Xu et al., "Intrinsic Wrench Estimation and Its Performance Index for Multisegment Continuum Robots," IEEE Transactions on Robotics, vol. 26, No. 3, pp. 555-561, Jun. 2010.
Xu et al., "System Design of an Insertable Robotic Effector Platform for Single Port Access (SPA) Surgery," in IEEE/RSJ International Conference on Intelligent Robots and Systems, 2009, pp. 5546-5552.
Xu, "Design, Modeling and Analysis of Continuum Robots as Surgical Assistants with Intrinsic Sensory Capabilities," Phd Thesis, Columbia University 2009.
Yamamoto et al., "Vitrectomy with or without arteriovenous adventitial sheathotomy for macular edema associated with branch retinal vein occlusion," Am J Ophthalmol, 2004, vol. 138, pp. 907-914.
Yamashita et al., "Handheld Laparoscopic Forceps manipulator Using Multi-slider Linkage Mechanisms," in MICCAI 2004 (7th International Conference on Medical Image Computing and Computer-Assisted Intervention), 2004, pp. 121-128.

Yoo et al., "Three-Dimensional Modeling and Visualization of the Cochlea on the internet," IEEE Transactions on Information Technology in Biomedicine, 2000, vol. 4, pp. 144-151.
Yoon et al., "A 4-dof flexible continuum robot using a spring backbone," in 2009 International Conference on Mechatronics and Automation, Aug. 2009, pp. 1249-1254.
Yoon et al., "Development of an Automated Steering Mechanism for Bladder Urothelium Surveillance," J. Med. Device., 2009, vol. 3, No. 1, p. 011004-1-011004-9.
Yoshikawa, "Force Control of Robot Manipulators," In 2000 IEEE International Conference on Robotics and Automation (San Francisco, CA, USA, 2000), No. Apr., pp. 220-226.
Yu et al., "Design, Calibration and Preliminary Testing of A Robotic Telemanipulator for OCT guided Retinal Surgery," In Accepted for publication in IEEE International Conference on Robotics and Automation (ICRA2013).
Yu et al., "Evaluation of microsurgical tasks with OCT-guided and/or robot-assisted ophthalmic forceps," Biomed. Opt. Express, 2015, vol. 6, No. 2, p. 457-472.
Yun et al., "A novel design and analysis of a 3-DOF parallel manipulator for micro/nano manipulation," in 2008 IEEE Workshop on Advanced robotics and Its Social Impacts, 2008, pp. 1-6.
Zanganeh et al., "The inverse kinematics of hyper-redundant manipulators using splines," Proc. 1995 IEEE Int. Conf. Robot. Autom., 1995, vol. 3, pp. 2797-2802.
Zghal et al., "Efficient gradient projection optimization for manipulators with multiple degrees of redundancy," in Robotics and Automation, 1990. Proceedings., 1990 IEEE International Conference on. IEEE, 1990, pp. 1006-1011.
Zhang et al., "A Pilot Study of Robot-Assisted Cochlear Implant Surgery Using Steerable Electrode Arrays," in International Conference on Medical Image Computing and Computer-Assisted Intervention (MICCAI '06), 2006, pp. 33-40.
Zhang et al., "Inroads towards Robot-Assisted Cochlear Implant Surgery using Steerable Electrode Arrays," Otology & Neurology special issue on Cochlear Implants, doi: 1097/MAO.0b013e3181e7117e, 2010.
Zhang et al., "Model and Parameter Identification of Friction During Robotic Insertion of Cochlear-Implant Electrode Arrays," in IEEE International Conference on Robotics and Automation, 2009, pp. 3859-3864.
International Search Report and Written Opinion for PCT Application No. PCT/US18/50948 dated Nov. 20, 2018 (8 pages).
Zhang et al., "Optimal Path Planning for Robotic Insertion of Steerable Electrode Arrays in Cochlear Implant Surgery," ASME Journal of Medical Devices, vol. 3, No. 1, 2009.
Zhang et al., "Path Planning and Workspace Determination for Robot-Assisted Insertion of Steerable Electrode Arrays for Cochlear Implant Surgery," Med Image Comput Comput Assist Interv. 2008;11(Pt 2):692-700.
Zhang, "Design of Steerable Electrode Arrays and Optimal Insertion Path Planning for Robot-Assisted Cochlear Implant Surgeries," Phd Thesis, Department of Mechanical Engineering, Columbia University, New York City, NY 2010.
Zhang, "Design of Underactuated Steerable Electrode Arrays for Optimal Insertions," J. Mech. Robot., vol. 5, No. 1, p. 011008, Jan. 2013.
Zhang, "Flexible camera calibration by viewing a plane from unknown orientations," Proc. Seventh IEEE Int. Conf. Comput. Vis., vol. 1, 1999, 8 pages.
Zheng et al., "Use of a distal ulnar artery perforator-based bilobed free flap for repairing complex digital defects," J. Hand Surg. Am., 2014, vol. 39, No. 11, pp. 2235-2242.
Zheng et al., Strategies for Automatic Assembly of Deformable Objects, IEEE International Conference on Robotics and Automation, 1991, pp. 2598-2603.
Zhou et al., "Linear Velocity and Acceleration Estimation of 3 DOF Haptic Interface," In IEEE International Workshop on Haptic Audio Visual Environments and their Application (HAVE 2008) (Ottawa, Canada, 2008), pp. 137-142.
Zlatanov et al., "A Unifying Framework for Classification and Interpretation of Mechanism Singularities," ASME J. of Mechanical Design, 1995, vol. 117, pp. 566-572.

(56) References Cited

OTHER PUBLICATIONS

Chiaverini et al., "Redundancy resolution for the human-arm-like manipulator", Robotics and Autonomous Systems 8, 1991, pp. 239-250.
Conrad et al., "Interleaved Continuum-Rigid Manipulation: An Augmented Approach For Robotic Minimally-Invasive Flexible Catheter-based Procedures", IEEE International Conference on Robotics and Automation, 2013, pp. 718-724.
Costello et al., Anatomical Studies of the neurovascular bundle and cavernosal nerves, BJU International, vol. 94, 2004, pp. 1071-1076.
Kim et al., "Interposition Sural Nerve Grafting During Radical Retropubic Prostatectomy", Urology, vol. 57, 2001, pp. 211-216.
Takenaka et al., "Anatomical Analysis of the Neurovascular Bundle Supplying Penile Cavernous Tissue to Ensure a Reliable Nerve Graft After Radical Prostatectomy", The Journal of Urology, vol. 172, 2004, pp. 1032-1035.
Turk et al., "Sural nerve graft during laparoscopic radical prostatectomy initial experience", Urologic Oncology, vol. 7, 2002, pp. 191-194.

\* cited by examiner

STEERABLE ENDOSCOPE WITH CONTINUUM MANIPULATOR

RELATED APPLICATIONS

This application claims the benefit of U.S. Provisional Patent Application No. 62/429,675, filed Dec. 2, 2016, entitled "DISPOSABLE ENDOSCOPE," and U.S. Provisional Patent Application No. 62/507,110, filed May 16, 2017, entitled "DISPOSABLE ENDOSCOPE." the entire contents of both of which are incorporated herein by reference.

STATEMENT REGARDING FEDERALLY SPONSORED RESEARCH OR DEVELOPMENT

This invention was made with government support under 4224513461 awarded by the National Science Foundation. The government has certain rights in the invention.

BACKGROUND

The present invention relates to a steerable endoscope and, in particular, systems and methods for adjusting a bending angle of an end-effector of an endoscope.

SUMMARY

Upper endoscopy or Esophagogastroduodenoscopy (EGD) is currently performed in an endoscopic unit, emergency department, or intensive care unit due to the equipment utilized and the administration of sedation with a need for patient monitoring. This limits broad primary patient access and exposes patients to sedation-related adverse events. If sedation can be avoided, bedside clinic-based EGD can be enabled for a host of applications (e.g., esophageal varices screening, gastroesophageal reflux disease non-responsive to medical therapy, suspected upper gastrointestinal (GI) tract bleeding, and dysphagia). In addition, traditional endoscopes require reprocessing between each use, thereby increasing cost of care, and effective operation of an endoscope requires long training due to a non-intuitive maneuvering/control mechanism.

To overcome these and other challenges, various embodiments of the invention provide an endoscope system with intrinsic pneumatic actuation. The endoscope system includes a user interface (e.g., an "actuator" or a "controller") using a continuum manipulator architecture and a steerable tip using parallel bellow actuators. Operation of this endoscope is intuitive in that bending movement of the steerable tip is controlled by a corresponding bending movement applied by the user to the user interface. In some implementations, three super-elastic NiTi backbones within the user interface are connected to the user's handle. The free ends of these backbones provide push-and-pull action for moving three corresponding syringe pistons. The pistons, in turn, displace air-filled tubes to expand/contract three corresponding parallel bellows in the steerable tip.

In one embodiment, the invention provides a steerable endoscope system including a continuum manipulator, a plurality of syringes, and a steerable tip. The continuum manipulator includes a plurality of spaced discs and a plurality of backbones each extending through all discs of the plurality of spaced discs. The continuum manipulator is configured such that a bending movement of the continuum manipulator changes a varying linear displacement of each backbone. Each backbone is further coupled to a different one of the plurality of syringes such that the linear displacement of each backbone pushes or pulls a piston of the corresponding syringe by a varying amount. The steerable tip includes a plurality of bellows each pneumatically coupled to a different syringe such that movement of the piston of a syringe causes the corresponding bellow to inflate or deflate by varying amounts. Because the distal end of each bellow is fixedly coupled to the same end effector, variations in the amount of inflation or deflation on each bellow causes a bending of the steerable tip.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
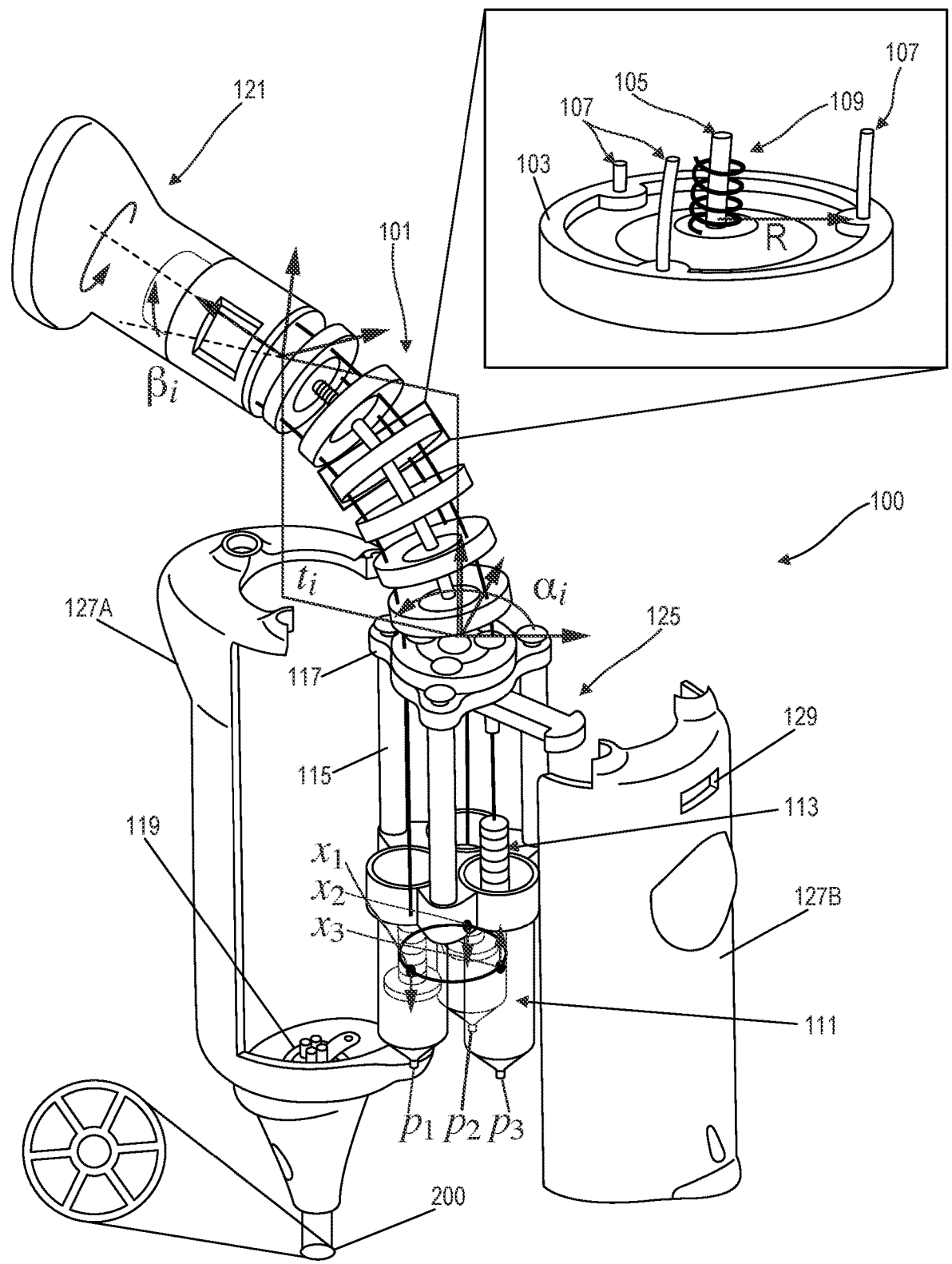
FIG. 1 is an exploded perspective view of an actuator for an endoscope according to one embodiment.

FIG. 1 illustrates an actuator 100 (or "controller") for an endoscope. By manipulating the actuator 100, a user is able to control a steerable tip of the endoscope that is coupled to the actuator 100 by a catheter, as described in further detail below. The actuator 100 includes a continuum manipulator 101. The continuum manipulator 101 includes a plurality of disks 103 arranged along a primary backbone 105. As shown in the insert of FIG. 1, a series of three secondary backbones 107 are arranged along a pitch circle with a radius R. Accordingly, each secondary backbone passes through an opening in each disc 103 at the same distance, R, from the opening through which the primary backbone 105 passes. A spring 109 is positioned coaxially around the primary backbone 105 as a spacer between the discs 103.

Each secondary backbone 107 is configured to slidably move through the opening of each disc 103 as described further below. In the example of FIG. 1, the primary backbone 105 is also configured to slidably move relative to each disc 103 through a center opening. However, the spring 109 maintains a spacing between the discs 103. Accordingly, when the continuum manipulator 101 is bent (for example, as shown in FIG. 1), the secondary backbones 107 will slidably move relative to the discs 103 causing one or more of the secondary backbones 107 to extend or retract relative to the distal end of the continuum manipulator 101. Such bending movements (or other movements such as, for example, linear pushing or pulling on the continuum manipulator 101) may also cause the primary backbone 105 to extend of retract relative to the distal end of the continuum manipulator 101. However, the springs 109 act on the discs 103 applying a force that urges the spacing between neighboring discs 103 to return to a relatively constant equilibrium spacing distance.

In some implementations, a single spring 109 runs the entire length of the continuum manipulator 101 with each disc 103 coupled to a particular location on the spring 109 due to the helical shape of the spring. In other implementations, separate individual springs 109 may be positioned between each set of neighboring discs 103. In still other implementations, the spring 109 may be omitted entirely and, instead, a fixed spacing distance between each disc 103 is maintained by fixedly coupling the primary backbone 105 to each disc 103 at locations along the length of the primary backbone 105. In other implementations, one or more additional springs may be positioned coaxial to each of the secondary backbones 107 such that the spring force of each additional spring counteracts a bending force applied to the continuum manipulator 101 and urging the continuum manipulator 101 to return to an equilibrium pose (e.g., where each of the backbones is straight).

Returning now to the example of FIG. 1, a distal end of each of the three secondary backbones 107 is coupled to a different one of three syringes 111. In this disclosure, the term "syringe" is used to refer to devices where a linear movement causes an increase or decrease in air or fluid pressure including, for example, a device where a piston is positioned within a cylinder and movement of the piston within the cylinder causes a change in an enclosed volume of the cylinder. In the example of FIG. 1, each secondary backbone 107 is coupled to a piston of the respective syringe 111 by a screw connector 113. A series of three spacing pillars 115 couple the syringes 111 to a base 117 at the distal end of the continuum manipulator 101. Accordingly, the outer bodies of the syringes 111 remain at a fixed distance from the continuum manipulator 101. However, as discussed in further detail below, linear movement ($x_1$, $x_2$, $x_3$) of each individual secondary backbone 107 pushes or pulls a piston of the corresponding syringe 111 relative to the outer body of the syringe 111. This displacement of the piston (caused by movement of the corresponding secondary backbone 107) generates a change in air pressure ($p_1$, $p_2$, $p_3$) for the corresponding syringe 111. Although, in the example of FIG. 1, the secondary backbones 107 are coupled to the pistons of the syringes 111 while the outer bodies of the syringes 111 are maintained at a stationary distance from the base 117 of the continuum manipulator 101, in other implementations, the secondary backbones 107 may instead be coupled to the outer bodies of the syringes 111 while the pistons of the syringes 111 are held at a stationary distance from the base 117.

The outlet of each syringe 111 is coupled to a catheter 200 by an adapter 119. As discussed in further detail below, the catheter 200 includes different lumens (or "pneumatic channel") for each syringe 111. Accordingly, movement of a piston into the corresponding outer body of a syringe 111 causes the syringe 111 to push air through the adapter 119 into the catheter 200 and, conversely, retracting the piston from the outer body of a syringe 111 cases the syringe 111 to pull air from the catheter into the syringe 111 through the adapter 119.

A handle 119 is coupled to a proximal end of the continuum manipulator 101. In the example of FIG. 1, the handle 119 is rotatably coupled to the continuum manipulator 101 by a bearing aligned with a longitudinal axis of the actuator 100. This rotatable coupling avoids mechanical lock due to possible twisting of the continuum manipulator 101. When using the actuator 100 to control the steerable tip of the endoscope, a user will hold the actuator by the handle 119 and bend the continuum manipulator relative to the base 117. This bending motion of the continuum manipulator 101 causes a change in the linear position of one or more of the secondary backbones 107 and, in turn, a change in the position of the piston of the corresponding syringe 111.

In the example of FIG. 1, a user can also pull the handle (e.g., linearly) away from the base 117 (causing the pistons in all syringes 111 to retract) or push the handle (e.g., linearly) towards the base 117 (causing the pistons in all syringes 111 to extend further). As discussed in further detail below, the pushing or pulling the handle (e.g., linearly) relative to the base 117 can be done to adjust a stiffness of the steerable tip and to provide for more controlled movements. The actuator 100 of FIG. 1 also includes a slider lock 125 positioned adjacent to (or incorporated into) the base 117. The slider lock 125 moves slidably in a linear direction perpendicular to the spacing pillars 115. When pushed toward the primary backbone 105 (extending from the distal end of the continuum manipulator 101 near the base 117), the slider lock 125 engages the primary backbone 105 by friction and prevents (or, in some implementations, restricts) linear movement of the primary backbone 105. Sliding the slider lock 125 away from the primary backbone 105 releases the primary backbone 105 restoring its ability for linear movement. In this way, when the "stiffness" of the continuum manipulator 101 and the steerable tip of the endoscope is adjusted by a user pushing or pulling the handle 121, the slider lock 125 can be slid into place to engage the primary backbone 105 and, thereby, maintain the desired level of stiffness. Accordingly, the continuum manipulator 101 of FIG. 1 can be moved with three degrees-of-freedom (DoF): two bending angles ($\alpha_i$ and $\beta_i$) and elongation ($l_i$).

The actuator 100 illustrated in FIG. 1 also includes an external housing 127 formed, in this example, as a pair of molded plastic housing sections 127A, 127B which are configured to engage by snap fit (or, in some implementations, by securing screws) to housing at least a portion of the actuator 100. In the example of FIG. 1, the external housing 127 encloses the syringes 111, the spacing pillars 115, and the base 117 of the continuum manipulator 101. The continuum manipulator 101 (and the handle 121) extends from an opening at the top of the housing 127 and the adapter 119 extends from an opening at the bottom of the housing 127. The slider lock 125 extends through an opening 129 in a side of the housing 127B.

In the example of FIG. 1, the primary backbone 105 is formed of 1.5 mm NiTi wire and the secondary backbones 107 are formed of 1.0 mm NiTi wire. The spring 109 is rated at 3.65 lbs/in and has a compressed length of up to 48% of its initial length. Each spacer disc 103 is 5.5 mm thick. The pitch radius (i.e., the distance between the primary backbone 105 and each secondary backbone 107 along each disc 103) is 12.5 mm. In other implementations, different material (with different sizes and/or ratings) may be used. However, in this example using these materials, a maximal bending angle $B_{i-max}$ of −24.64 can be calculated using the equation:

$$x_j = \pm R(\beta_{i-rest} - \beta_{i-max}); j=1, 2, 3 \quad (1)$$

where $x_j = \pm 25$ mm, pitch radius R=12.5 mm, and $\beta_{i-rest} = \pi/2$. Considering compressibility of the spring along the primary backbone 105, the length of the continuum manipulator 101 at rest is such that, when the springs are fully compressed, it reaches a positive 25 mm displacement.

Figure 2:
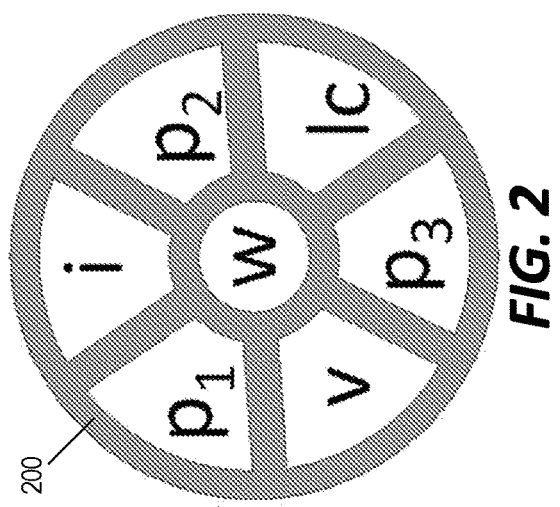
FIG. 2 is a cross-sectional view of an endoscope catheter for use with the actuator of FIG. 1.

As discussed above, the actuator 100 couples to a catheter 200 at the adapter 119. In some implementations, the adapter 119 is configured to permanently couple the actuator 100 to a catheter 200 (for example, by a threaded screw fitting) to allow the catheter to be replaced or exchanged for different uses and applications. FIG. 2 illustrates an example of a catheter 200 configured for use with the actuator 100. The catheter 200 may be formed of a material such as, for example, NuSil MED-4880 silicone. As shown in cross-section in the example of FIG. 2, the catheter 200 includes seven different lumens (or "channels"). A central lumen (labeled as w in FIG. 2) embeds a wire rope in the catheter 200 to increase axial stiffness of the catheter 200. Three of the lumens (labelled as $p_1$, $p_2$, and $p_3$ in FIG. 2) are pneumatic channels each extending between a different one of the syringes 111 of the actuator 100 and a corresponding bellow of the steerable tip (discussed further below).

The video lumen (labelled v in FIG. 2) is used for electrical and data wiring to a camera positioned at the tip of the endoscope. A fluid channel (labelled lc in FIG. 2) is used to run water for cleaning a lens of the camera at the tip of the endoscope while in use. The last channel (labelled i in FIG. 2) is an insufflation channel with an opening at the base of the steerable tip. It is again noted that the catheter 200 of FIG. 2 is just one example of a catheter for use with the actuator 100 of FIG. 1. In other implementations, the catheter 200 may be configured to include more, fewer, or different lumens or different shapes, sizes, and configurations. Furthermore, in the example of FIG. 1, the actuator 100 does not show opening or other structures for coupling to the proximal end of the video lumen v, the fluid lumen lc, or the insufflation lumen i. However, in some implementations, couplings for the proximal end of these (or other) channels may be provided, for example, by the adapter 119 extending from the bottom of the housing 127 of the actuator 100 or may be incorporated into the actuator 100 itself.

Figure 3:
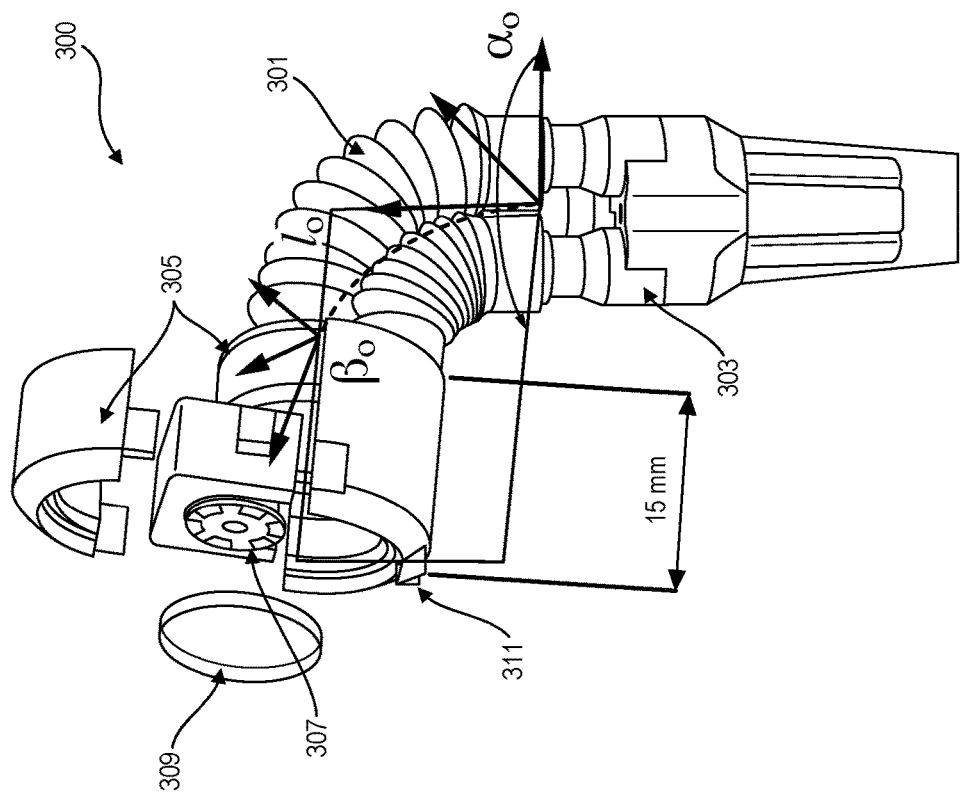
FIG. 3 is an exploded perspective view of a steerable tip of an endoscope controlled by the actuator of FIG. 1.

FIG. 3 illustrates an example of a steerable tip 300 positioned at a distal end of the endoscope and coupled (or couplable) to the actuator 100 by the catheter 200. In this example, the steerable tip 300 includes a series of three bellow 301. In this example, the bellows 301 are constructed of a rubber material and each has a nominal diameter of 5.6 mm, a maximal length of 29 mm, and a minimal length of 14 mm. The bellows 301 are arranged as the vertices of an equilateral triangle. Each individual bellow 301 is pneumatically coupled to a different corresponding syringe 111 by a pneumatic channel of the catheter 200. A tip adapter 303 pneumatically couples each individual bellow 301 to a different pneumatic channel of the catheter 200.

The steerable tip 300 also includes a tip housing 305 positioned at a distal end of the bellows 301. In the example of FIG. 3, the tip housing 305 is again formed as a pair of molded plastic housing components that snap-fit to enclose the components at the distal tip. In particular, a camera 307 is positioned at the distal tip and enclosed by the tip housing 305. In this example, the camera includes a 720×576 pixel camera (RA78080A-60LED Bangu Technology Development Co., Baoan, China). The tip housing 305 also holds and positions a lens 309 (e.g., a sapphire lens) for the camera 307 in the field of view of the camera 307 which, among other things, provides waterproofing for the camera 307. A cleaning nozzle 311 extends from the tip housing 305 and is positioned and configured to dispense water on the lens 309 to clean the lens 309 during use. The tip adapter 303 also provides for coupling wires for the camera 307 and fluid channels for the cleaning nozzle 311 to the respective lumen of the catheter 200.

Figure 4:
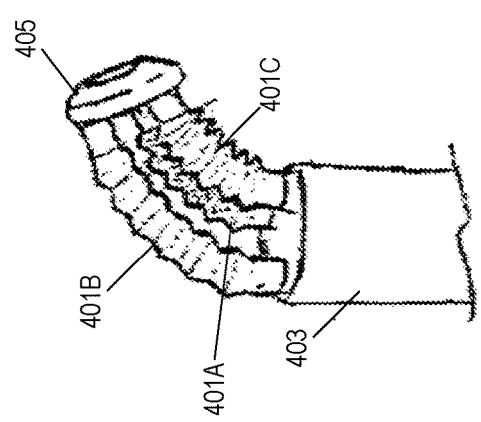
FIG. 4 is a perspective view of another example of a steerable tip of an endoscope controllable by the actuator of FIG. 1.

FIG. 4 illustrates another, simplified example of a distal tip for use with the actuator 100 of FIG. 1. This example shows only the three bellows 401A, 401B, 401C coupled between a catheter 403 and an end effector 405. When a piston of a syringe 111 moves, it creates air pressure that pushes or pulls air through the pneumatic channel of the catheter into an individual bellow (e.g., 401A, 401B, or 401C). This causes that particular bellow to extend or retract accordingly. The comparative extension and retraction of each of the three bellows 401A, 401B, 401C causes the end effector 405 to bend (as shown in FIG. 4). The steerable tip 300 of FIG. 3 operates in this same way. Because the bellows can be independently extended/contracted using the pneumatic pressures $p_1$, $p_2$, $p_3$, the movement of the steerable tip 300 can be controlled with three degrees-of-freedom (DoF): two tilting angles ($\alpha_0$ and $\beta_0$ illustrated in FIG. 3) and an elongation ($l_0$ in FIG. 3).

Figure 5:
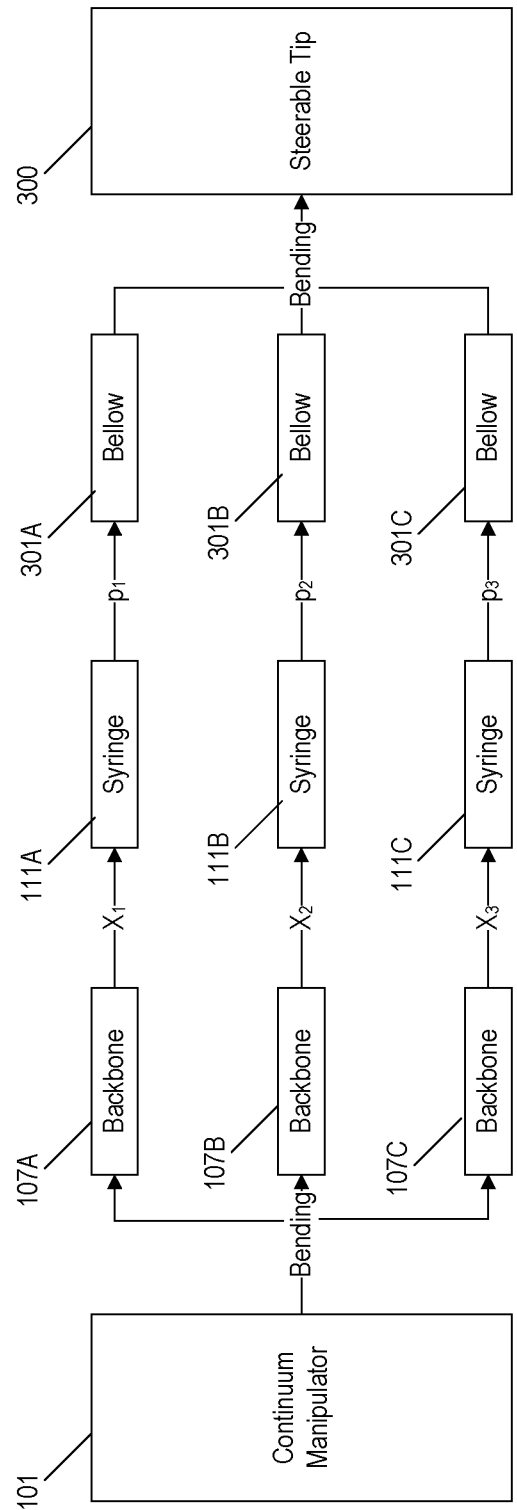
FIG. 5 is a schematic flowchart of a method for controlling the steerable tip of FIG. 3 using the actuator of FIG. 1.

FIG. 5 provides a schematic illustration of how the bending of the continuum manipulator 101, the secondary backbones 107A, 107B, 107C, the pistons of the syringes 111A. 111B, 11C, and the bellows 301A, 301B, 301C interact to provide for controlled bending (or "steering") of the steerable tip 300. As discussed above, bending of the continuum manipulator 101 by a user causes a change in the linear position x1, x2, x3 of one or more secondary backbone 107A, 107B, 107C. Due to the fixed coupling of the distal end of each secondary backbone 107A, 107B, 107C to a corresponding syringe 111A, 111B, 111C, the changes in the linear position x1, x2, x3 of each secondary backbone 107A, 107B, 107C acts on the corresponding syringe 111A, 111B, 111C and, thereby, causes a corresponding change in the air pressure p1, p2, p3 of each syringe 111A, 111B, 111C. This type of change in pressure in any one of the syringes 111A, 111B, 111C pumps air into or out of the corresponding bellow 301A, 301B, 301C through the corresponding pneumatic channel of the catheter 200.

Because each syringe is coupled to a different one of the bellows (forming three separate pneumatic systems), different changes in the linear position of the secondary backbones 107A, 107B. 107C results in different magnitudes of inflation or deflation in the corresponding bellows 301A, 301B, 301C. Because all three of the bellows 301A, 301B, 301C are fixedly coupled between the tip adapter 303 and the tip housing 305, variations in the magnitude of inflation or deflation causes the steerable tip 300 to bend at the bellows 301A, 301B, 301C.

For example, as the handle 121 is moved to bend the continuum manipulator 101 from a straight position into the bent position illustrated in FIG. 1, the two secondary backbones 107 towards the left of the image in FIG. 1 are pushed further into their corresponding syringes 111 and the secondary backbone 107 towards the right side of the image is pulled away from its corresponding syringe 111. Returning to FIG. 5, consider a similar bending motion of the continuum manipulator 101 which cause backbone 107A and backbone 107B to extend further into syringe 111A and syringe 111B, respectively, while also causing backbone 107C to retract away from the syringe 111C. This particular set of changes in linear position of the secondary backbones 107A, 107B, 107C causes syringe 111A to push air into bellow 301A, causes syringe 111B to push air into bellow 301B, and causes syringe 111C to pull air out of bellow 301C. As a result, bellows 301A and 301B are further inflated while bellow 301C is further deflated. This particular set of inflations and deflations of the bellows 301A, 301B, and 301C causes the steerable tip 300 to bend as shown in the example of FIG. 3.

Figure 6A:
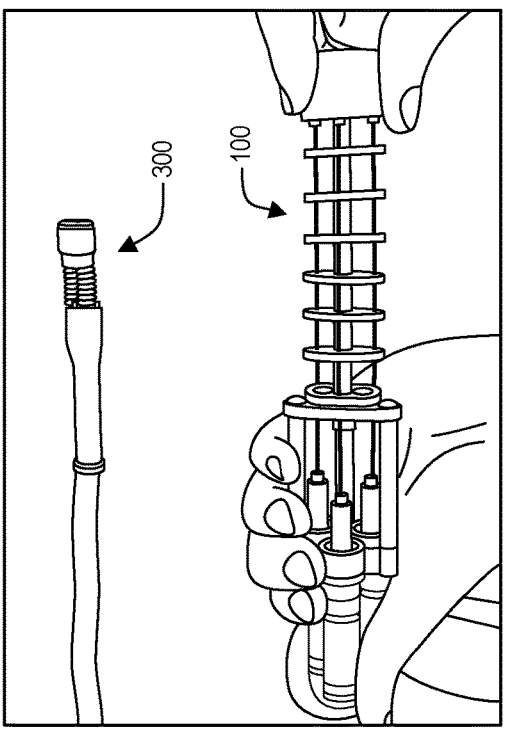
FIGS. 6A, 6B. 6C, and 6D are overhead views of the steerable tip of FIG. 3 and the actuator of FIG. 1 showing various positions of the actuator and a corresponding position of the steerable tip.
Figure 6B:
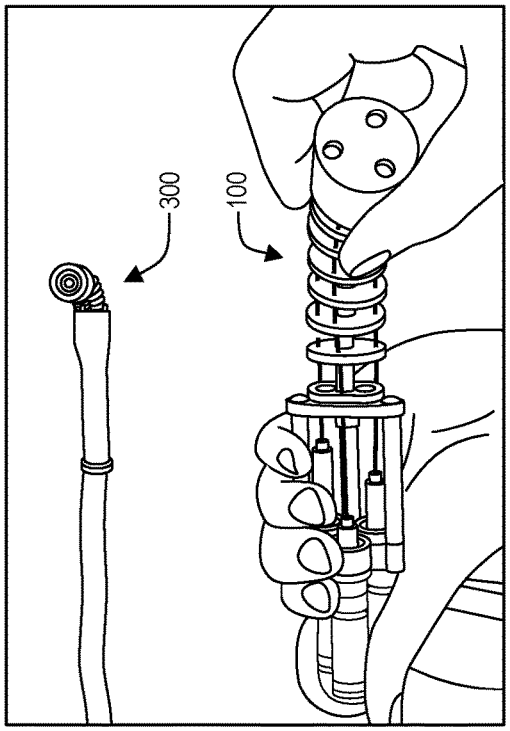
Figure 6C:
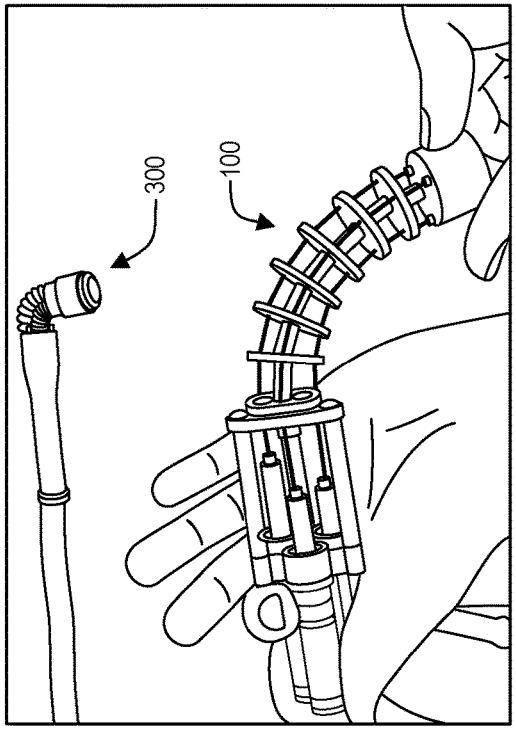
Figure 6D:
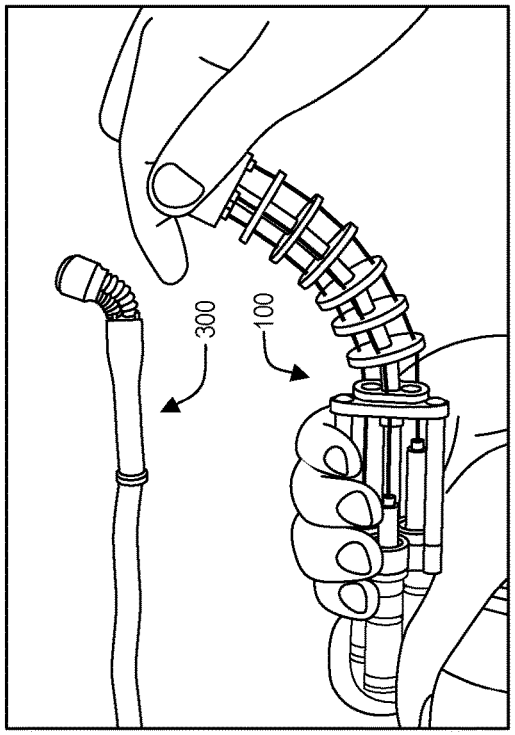

Accordingly, in the system illustrated in FIGS. 1, 2, and 3, a bending movement applied by a user to the continuum manipulator 101 of the actuator 100 causes a corresponding bending movement of the steerable tip 300. FIGS. 6A, 6B, 6C, and 6D illustrate further examples of bending movement applied by a user to the actuator 100 and the resulting corresponding bending movement exhibited by the steerable tip 300. In FIG. 6A, the actuator 100 is held straight. As a result, the bellows of the steerable tip 300 are equally inflated and the steerable tip does not bend in any direction. In the example of FIG. 6B, the actuator 100 is bent upward and, as a result, the bellows of the steerable tip 300 are correspondingly inflated or deflated causing the steerable tip 300 to also bend upwards. In the example of FIG. 6C, the actuator 100 is bent backwards and, as a result, the corresponding inflation/deflation of the bellows cause the steerable tip 300 to also bend backwards. Finally, in the example of FIG. 6D, the actuator 100 is bent forwards and, as a result, the corresponding inflation/deflation of the bellows cause the steerable tip 300 to also bend forward.

The corresponding bending movements of the steerable tip 300 and the continuum manipulator 101 of the actuator 100 exhibits an intrinsic mapping. The scaling factor between input movements performed on the actuator 100 (i.e., $\alpha_i$, $\beta_i$, $l_i$) and resulting movements of the steerable tip 300 (i.e., $\alpha_o$, $\beta_o$, $l_o$) can be defined, for example, by the size and dimensions of the syringes 111 of the actuator 100. In some implementations, the actuator 100 is configured to allow a user to selectively change the syringes 111 to adjust the scalability. In some implementations configured for interchangeable syringe configurations, a set of syringes is provided with a common stroke (e.g., 53 mm) and different diameters. The actuator 100 is also configured to selectively couple the syringes into syringe holders or brackets positioned equidistantly along the circumference of a pitch circle (e.g., with a radius of 12.5 mm) to accommodate different syringe diameters.

Figure 7A:
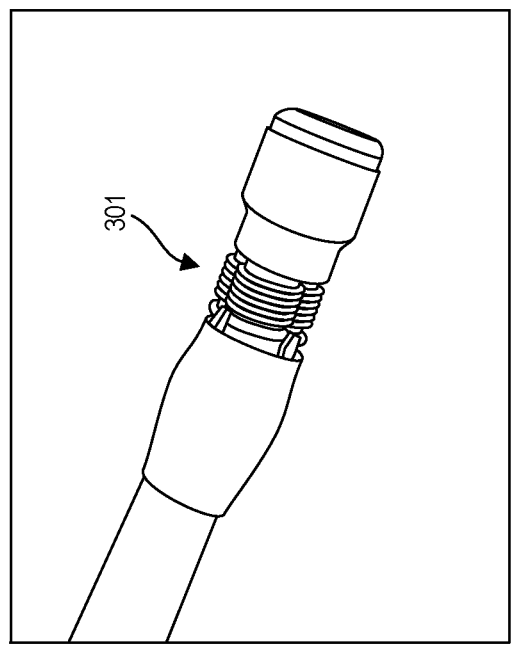
FIGS. 7A and 7B are perspective views of the steerable tip of FIG. 3 in two different modes of operation including a mode of operation where the stiffness of the tip is increased to limit movement of the steerable tip.
Figure 7B:
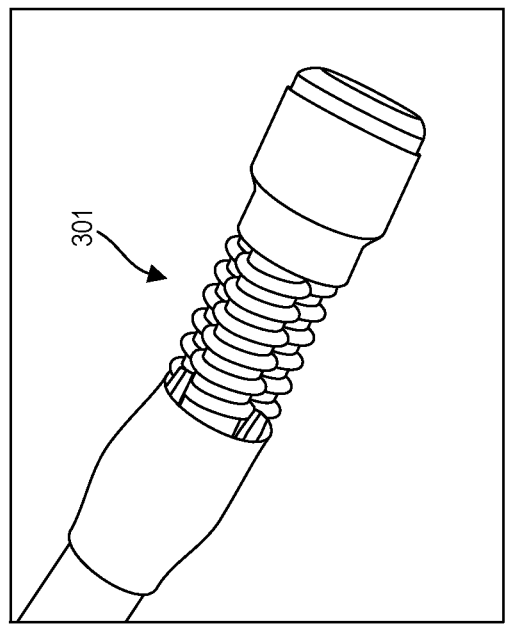

As discussed above, in the example of FIG. 1, a user can also pull or push the handle in a substantially linear direction relative to the base of the actuator 100 to cause all of the secondary backbones to move in the same direction towards or away from their corresponding syringes. FIGS. 7A and 7B illustrate that corresponding effect that this type of movement of the actuator 100 causes at the steerable tip 300. In FIG. 7A, all three of the bellows 301 are similarly deflated. This is caused by pulling the handle of the actuator 100 away from the base of the actuator 100. Conversely, FIG. 7B shows all three of the bellows 301 similarly inflated. This is caused by pushing the handle of the actuator 100 towards the base of the actuator 100 (for example, returning the handle and, in turn, the primary backbone to its original linear position after pulling the handle to cause the situation of FIG. 7A).

Pulling the handle of the actuator 100 to deflate all of the bellows 301 (as shown in FIG. 7A) increases the stiffness of the tip and can be used when inserting the endoscope tip into the upper gastrointestinal tract (UGI). This manipulation also makes the actuator 100 and, in turn, the steerable tip 300 more resistant to bending. Accordingly, a user might increase the stiffness in this way in order to make smaller adjustments to the bending position of the steerable tip 300.

Although the examples described above include a "pneumatic" system where air pressure changes via the syringe cause a corresponding bellow to inflate or deflate with air, in some implementations, the syringe and bellow are communicative coupled by a fluid medium (e.g., a "hydraulic" system). Accordingly, the pneumatic channels of the conduits discussed in reference to FIG. 2 above can be replaced in some embodiments with a fluid channel. The phrase "pressure medium channel" as used herein is understood to include a pneumatic channel or a fluid-based channel.

Thus, the invention provides, among other things, an endoscope system including an actuator and a steerable tip configured to control bending of the steerable tip by a corresponding bending of a continuum manipulator of the actuator. Various features and advantages of the invention are set forth in the following claims.

What is claimed is:

1. A steerable endoscope system comprising:
   a continuum manipulator including
      a plurality of spaced discs each including a plurality of backbone openings, and
      a plurality of backbones, each including a proximal end fixedly coupled to a proximal end of the continuum manipulator and a distal end slidably extending beyond a distal end of the continuum manipulator, wherein each backbone of the plurality of backbones slidably extends through a backbone opening of each disc of the plurality of spaced discs,
      wherein the continuum manipulator is configured such that a bending movement of the continuum manipulator changes a linear displacement of the distal end of each backbone of the plurality of backbones extending from the distal end of the continuum manipulator;
   a plurality of syringes coupled to the continuum manipulator, wherein each syringe of the plurality of syringes is coupled to the distal end of a different one of the plurality of backbones such that linear displacement of a backbone in a first direction pushes a piston of the syringe and linear displacement of the backbone in a second direction pulls the piston of the syringe, wherein either the piston of the syringe or an outer body of the syringe is fixedly coupled relative to the distal end of the continuum manipulator;
   a steerable tip including an end effector and a plurality of bellows, the end effector including a distal end and a proximal end, wherein each bellow of the plurality of bellows is pneumatically coupled to a different syringe of the plurality of syringes such that movement of the piston of a syringe in the first direction causes inflation of a bellow of the plurality of bellows and movement of the piston of the syringe in the second direction causes deflation of the bellow;
   a primary backbone extending through each disc of the plurality of spaced discs, wherein the plurality of backbones includes a plurality of secondary backbones, and wherein the plurality of backbone openings of each disc of the plurality of spaced discs includes a primary backbone opening positioned at a center of the disc and a plurality of secondary backbone openings positioned around the primary backbone opening at a defined radius from the primary backbone opening; and a handle coupled to the continuum manipulator at the proximal end of the continuum manipulator, wherein a proximal end of the primary backbone is fixedly coupled to the proximal end of the continuum manipulator, wherein a distal end of the primary backbone slidably extends beyond the distal end of the continuum manipulator, and wherein the continuum manipulator is configured such that an external linear force applied to the handle in the second direction increases a stiffness of the steerable tip by causing all bellows of the plurality of bellows to deflate, wherein a distal end of each bellow of the plurality of bellows is fixedly coupled to the proximal end of the end effector such that inflation variations in the plurality of bellows causes a bending of the steerable tip.

2. The steerable endoscope system of claim 1, further comprising:

an actuator including the continuum manipulator and the plurality of syringes; and a catheter, wherein the catheter includes a plurality of internal pressure-medium channels, wherein the actuator is coupled to the distal tip by the catheter, and wherein the plurality of syringes is coupled to the plurality of bellows by the plurality of internal pressure-medium channels of the catheter.

3. The steerable endoscope system of claim 2, wherein the pressure-medium channels are pneumatic channels and wherein each syringe is pneumatically coupled to a corresponding bellow.

4. The steerable endoscope system of claim 2, wherein the pressure-medium channels include fluid-pressure channels and wherein each syringe is configured to inflate or deflate a corresponding bellow by applying a fluid pressure to the bellow through a fluid-pressure channel.

5. The steerable endoscope system of claim 1, wherein the catheter further includes an instrument channel extending from the actuator to the steerable tip.

6. The steerable endoscope system of claim 1, wherein the handle is coupled to the proximal end of the continuum manipulator by a bearing configured to allow rotation of the handle about a linear axis of the continuum manipulator.

7. The steerable endoscope system of claim 1, further comprising a slidable lock positioned near the distal end of the continuum manipulator and slidable in a direction perpendicular to the distal end of the primary backbone extending from the distal end of the continuum manipulator, wherein the slidable lock is configured such that sliding the slidable lock in a direction towards the primary backbone causes the slidable lock to frictionally engage the primary backbone and restrict linear movement of the primary backbone.

8. The steerable endoscope system of claim 1, wherein the continuum manipulator further includes a helical spring positioned coaxially around the primary backbone, wherein the primary backbone slidably extends through each disc of the plurality of spaced discs, and wherein the helical spring maintains a spacing between at least two discs of the plurality of spaced discs.

9. The steerable endoscope system of claim 1, wherein the bending of the steerable tip is proportionally scaled relative to the bending movement of the continuum manipulator.

10. The steerable endoscope system of claim 9, wherein the plurality of syringes includes a first plurality of syringes, wherein each syringe of the first plurality of syringes has a first piston stroke length and a first volume.

11. A method of operating the steerable endoscope of claim 1, comprising bending the steerable tip by applying a bending force to the continuum manipulator.

12. The method of claim 11, further comprising changing a bending angle of the steerable tip by changing an angle of the bending force applied to the continuum manipulator.

13. The method of claim 11, further comprising increasing a magnitude of bending of the steerable tip by adjusting the bending force applied to the continuum manipulator to increase a magnitude of the bending of the continuum manipulator.

14. The method of claim 11, further comprising increasing a stiffness of the steerable tip by applying a pulling force to the proximal end of the continuum manipulator which causes all bellows of the plurality of bellows to deflate.

15. A steerable endoscope system comprising:

a continuum manipulator including a plurality of spaced discs each including a plurality of backbone openings, and a plurality of backbones each including a proximal end fixedly coupled to a proximal end of the continuum manipulator and a distal end extending from a distal end of the continuum manipulator, wherein each backbone of the plurality of backbones slidably extends through a backbone opening of each disc of the plurality of spaced discs, wherein the continuum manipulator is configured such that a bending movement of the continuum manipulator changes a linear displacement of the distal end of each backbone of the plurality of backbones extending from the distal end of the continuum manipulator;

a plurality of syringes coupled to the continuum manipulator, wherein each syringe of the plurality of syringes is coupled to the distal end of a different one of the plurality of backbones such that linear displacement of a backbone in a first direction pushes a piston of the syringe and linear displacement of the backbone in a second direction pulls the piston of the syringe;

a steerable tip including an end effector and a plurality of bellows, wherein each bellow of the plurality of bellows is pneumatically coupled to a different syringe of the plurality of syringes such that movement of the piston of a syringe in the first direction causes inflation of a bellow of the plurality of bellows and movement of the piston of the syringe in the second direction causes deflation of the bellow, wherein a distal end of each bellow of the plurality of bellows is fixedly coupled to the end effector such that inflation variations in the plurality of bellows causes a bending of the steerable tip;

wherein the bending of the steerable tip is proportionally scaled relative to the bending movement of the continuum manipulator, wherein the plurality of syringes includes a first plurality of syringes, wherein each syringe of the first plurality of syringes has a firsts piston stroke length and a first volume; and a second plurality of syringes, wherein each syringe of the second plurality of syringes has a second piston stroke length and a second volume, wherein the second plurality of syringes are selectively interchangeable with the first plurality of syringes, and wherein interchanging the second plurality of syringes for the first plurality of syringes alters a proportional scalability of the bending of the steerable tip relative to the bending movement of the continuum manipulator.

* * * * *

UNITED STATES PATENT AND TRADEMARK OFFICE
CERTIFICATE OF CORRECTION

| | | |
|---|---|---|
| PATENT NO. | : 11,793,394 B2 | Page 1 of 1 |
| APPLICATION NO. | : 16/465621 | |
| DATED | : October 24, 2023 | |
| INVENTOR(S) | : Nicolo Garbin et al. | |

It is certified that error appears in the above-identified patent and that said Letters Patent is hereby corrected as shown below:

In the Specification

Column 1, Line 16:
Replace the following paragraph:
[[This invention was made with government support under 4224513461 awarded by the National Science Foundation. The government has certain rights in the invention.]]

With the paragraph:
--This invention was made with government support under grant number EB018992, awarded by the National Institutes of Health. The government has certain rights in the invention.--

Signed and Sealed this
Eighth Day of October, 2024

Katherine Kelly Vidal
*Director of the United States Patent and Trademark Office*